United States Patent [19]

Ogawa et al.

[11] Patent Number: 5,114,737

[45] Date of Patent: May 19, 1992

[54] PROCESS FOR PREPARING AN ORGANIC MONOMOLECULAR FILM

[75] Inventors: Kazufumi Ogawa, Hirakata; Norihisa Mino, Settsu, both of Japan

[73] Assignee: Matsushita Electric Industrial Co., Ltd., Osaka, Japan

[21] Appl. No.: 651,069

[22] Filed: Feb. 5, 1991

[30] Foreign Application Priority Data

Feb. 5, 1990 [JP] Japan ............... 2-25415
Feb. 5, 1990 [JP] Japan ............... 2-25416

[51] Int. Cl.$^5$ .............................................. B05D 3/06
[52] U.S. Cl. ................................. 427/36; 427/38; 427/44; 427/385.5
[58] Field of Search ............ 427/38, 44, 36, 54.1, 427/385.5

[56] References Cited

U.S. PATENT DOCUMENTS 4,715,929 12/1987 Ogawa ..................... 156/643
4,992,300 2/1991 Ogawa et al. ............. 427/38 X

FOREIGN PATENT DOCUMENTS 0249457 12/1987 European Pat. Off. .

Primary Examiner—Michael Lusignan
Attorney, Agent, or Firm—Panitch Schwarze Jacobs & Nadel

[57] ABSTRACT

A monomolecular polymer film or a lamination of monomolecular polymer films having polyacetylenic, polydiacetylenic, or polyacenic bonds is provided. The film or the lamination is prepared by the use of a chemical adsorbent having at least one triple bond, and a —SiCl group at one molecular end. The chemical adsorbent is adsorbed on a base plate and the polymerization is carried out by the predetermined method. Particularly, a highly oriented polymerized monomolecular film or a lamination is prepared by the use of e.g., the STM writing technique or the rubbing process.

105 Claims, 11 Drawing Sheets

  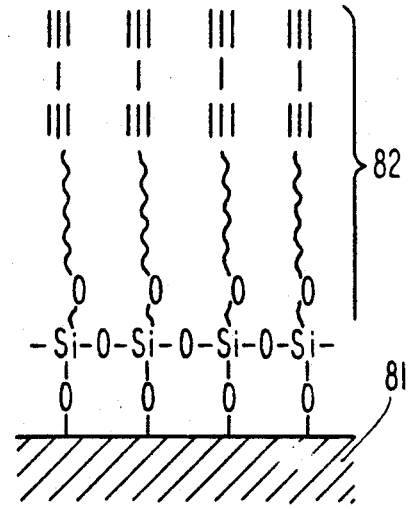
Fig. 8a  Fig. 8b  Fig. 8c
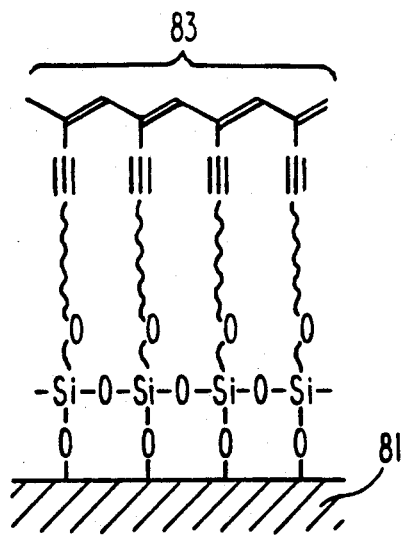 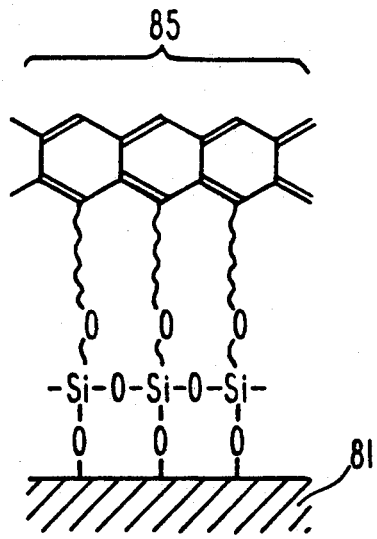
Fig. 8d  Fig. 8e

PROCESS FOR PREPARING AN ORGANIC MONOMOLECULAR FILM

BACKGROUND OF THE INVENTION

1. Field of the Invention

The present invention relates to a process for preparing an organic monomolecular film. In particular, this invention relates to a process for preparing an organic monomolecular polymer film having polyacetylenic, polydiacetylenic or polyacenic bonds, which exhibits electric conductivity and nonlinear optical effects.

2. Description of the Prior Art

Acetylene and diacetylene derivative polymers have electric conductivity because of the presence of a $\pi$-electron conjugated system, especially diacetylene derivative polymers have a nonlinear optical effect. Thus, these polymers are useful as optical or electronic functional materials such as optical recording media.

Generally, polymers of acetylene or diacetylene derivatives can be prepared by the polymerization method of Shirakawa et al., using the Ziegler-Natta catalyst. These polymers are obtained in a mass, and thus the direction of the polymerization is not regulated (i.e., the polymers have a three dimensional structure). Therefore, if a thin film is sliced from the polymer mass, the film cannot be an electronic functional material because a long conjugated system of $\pi$-electrons is not present in the polymer film. An organic monomolecular film having polyacetylenic bonds is considered to be prepared by a process which comprises forming a monomolecular film made of a straight hydrocarbon chain having an acetylene group on a base plate according to the LB (Langmuir-Blodgett) technique, and then polymerizing the hydrocarbon molecule at the acetylene group with a catalyst.

However, the organic monomolecular films prepared by this process are not stable to heat and ultraviolet radiation. Also, because the films have poor adhesiveness to the base plate, they are susceptible to peeling from the base plate when they are worked. Moreover, the direction of the polymerization of each molecule in the films is not regulated, so that a long conjugated system of $\pi$-electron is not present in the film. Therefore these films do not provide optical or electronic functional materials of high quality.

SUMMARY OF THE INVENTION

A process for preparing an organic monomolecular film of this invention, which overcomes the above-discussed and numerous other disadvantages and deficiencies of the prior art, comprises:

forming a monomolecular film on the surface of a base plate by adsorbing a chemical adsorbent having at least one triple bond, and a —SiCl group at one molecular end, and irradiating said monomolecular film with a high energy beam such as X-rays, gamma-rays, electron beam, or ion beam under an inert atmosphere to polymerize said chemical adsorbent at the triple bond, thereby forming a highly oriented conjugated polymer having polyacetylenic bonds.

A further embodiment of the present invention is a process for preparing an organic monomolecular film comprising:

forming a monomolecular film on the surface of a base plate by adsorbing a chemical adsorbent having at least one triple bond, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the triple bond of the chemical adsorbent adsorbed in the exposed portion, and irradiating said exposed or written monomolecular film with a high energy beam such as X-rays, gamma-rays, electron beam, or ion beam under an inert atmosphere to polymerize the remaining chemical adsorbent adsorbed in the unexposed portion, thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having at least one triple bond, and a —SiCl group at one molecular end, rubbing said monomolecular film to orient (i.e., align) said chemical adsorbent molecules, and irradiating said oriented monomolecular film with a high energy beam such as X-rays, gamma-rays, electron beam, or ion beam under an inert atmosphere to polymerize said chemical adsorbent at the triple bond, thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, and irradiating said monomolecular film with a low energy beam such as UV light to polymerize said chemical adsorbent at the diacetylene group, thereby forming a highly oriented conjugated polymer having polydiacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, and irradiating said exposed or written monomolecular film with a low energy beam such as UV light under an inert atmosphere to polymerize the remaining chemical adsorbent adsorbed in the unexposed portion, thereby forming a highly oriented conjugated polymer having polydiacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, rubbing said monomolecular film to orient (i.e., align) said chemical adsorbent molecules, and irradiating said oriented monomolecular film with a low energy beam such as UV light under an inert atmosphere to polymerize said chemical adsorbent at the diacetylene group, thereby forming a highly oriented conjugated polymer having polydiacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, and irradiating said monomolecular film with a high energy beam to polymerize said chemical adsorbent at the diacetylene group, thereby forming a highly oriented conjugated polymer having polydiacetylenic or polydiacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, and irradiating said exposed or written monomolecular film with a high energy beam such as X-rays, gamma-rays, electron beam, or ion beam under an inert atmosphere to polymerize the remaining chemical adsorbent adsorbed in the unexposed portion, thereby forming a highly oriented conjugated polymer having polyacetylenic or polydiacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, rubbing said monomolecular film to orient (i.e., align) said chemical adsorbent molecules, and irradiating said oriented monomolecular film with a high energy beam such as X-rays, gamma-rays, electron beam, or ion beam under an inert atmosphere to polymerize said chemical adsorbent at the diacetylene group, thereby forming a highly oriented conjugated polymer having polyacetylenic or polydiacetylenic bonds.

A still further embodiment of the present invention is a process for preparing an organic monomolecular film comprising:

forming a monomolecular film on the surface of a base plate by adsorbing a chemical adsorbent having at least one triple bond, and a —SiCl group at one molecular end, subjecting said monomolecular film to come into contact with a metal compound catalyst dissolved in an organic solvent to polymerize said chemical adsorbent at the triple bond, thereby forming a highly oriented conjugated polymer having a polyacetylenic bonds.

A still further embodiment of the present invention is a process for preparing an organic monomolecular film comprising:

forming a monomolecular film on the surface of a base plate by adsorbing a chemical adsorbent having at least one triple bond, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the triple bond of the chemical adsorbent adsorbed in the exposed portion, and subjecting said monomolecular film to come into contact with a metal compound catalyst dissolved in an organic solvent to polymerize the remaining chemical adsorbent adsorbed in the unexpected portion thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having at least one triple bond, and a —SiCl group at one molecular end, rubbing said monomolecular film to orient (i.e., align) said chemical adsorbent molecules, and subjecting said monomolecular film to come into contact with a metal compound catalyst dissolved in an organic solvent to polymerize said chemical adsorbent at the triple bond, thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, and subjecting said monomolecular film to come into contact with a metal compound catalyst dissolved in an organic solvent to polymerize said chemical adsorbent at the diacetylene group, thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, and subjecting said exposed monomolecular film to come into contact with a metal compound catalyst dissolved in an organic solvent to polymerize the remaining chemical adsorbent adsorbed in the unexposed portion, thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, rubbing said monomolecular film to orient (i.e., align) said chemical adsorbent molecules, and subjecting said oriented monomolecular film to come into contact with a metal compound catalyst dissolved in an organic solvent to polymerize said chemical adsorbent at the diacetylene group, thereby forming a highly oriented conjugated polymer having polyacetylenic bonds.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, subjecting said monomolecular film to come into contact with a metal compound catalyst dissolved in an organic solvent to polymerize said chemical adsorbent at the diacetylene group, thereby forming a polyacetylenic bonds in trans configuration, irradiating said catalyst-treated monomolecular film with a high energy beam under an inert atmosphere to produce further polymerization, thereby forming a highly oriented polyacene-type conjugated polymer.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, subjecting said exposed monomolecular film to come into contact with a metal compound catalyst dissolved in an organic solvent to polymerize the remaining chemical adsorbent adsorbed in the unexposed portion, having the diacetylene group, thereby forming a polyacetylenic bonds in trans configuration, and irradiating said catalyst-treated monomolecular film with a high energy beam under an inert atmosphere to produce further polymerization, thereby forming a highly oriented polyacene-type conjugated polymer.

A still further embodiment of the present invention is a process for preparing an organic monomolecular film comprising:

forming a monomolecular film on the surface of a base plate by adsorbing a chemical adsorbent having a diacetylene group, and a —SiCl group at one molecular end, rubbing said monomolecular film to orient (i.e., align) said chemical adsorbent molecules, subjecting said oriented monomolecular film to come into contact with a metal compound catalyst dissolved in an organic solvent to polymerize said chemical adsorbent at the diacetylene group, thereby forming polyacetylenic bonds in trans configuration, and irradiating said catalyst-treated monomolecular film with a high energy beam under an inactive atmosphere to produce further polymerization, thereby forming a highly oriented polyacene-type conjugated polymer.

Thus, the invention described herein makes possible the objectives of:

(1) providing a process for preparing an organic monomolecular film or lamination of monomolecular films having polyacetylenic or polydiacetylenic bonds, which is stable to heat and ultraviolet radiation;

(2) providing a process for preparing an organic monomolecular film or lamination of monomoleculer films having polyacetylenic or polydiacetylenic bonds, which has excellent adhesiveness to a base plate, thereby not being peeled from the base plate easily;

(3) providing a process for preparing an organic monomolecular film or lamination of monomolecular films having polyacetylenic or polydiacetylenic bonds, said bonds extending in a certain direction;

(4) providing a process for preparing an organic monomolecular film or lamination of monomolecular films having polyacetylenic or polydiacetylenic bonds, which is applicable for use as an optical or electronic functional material of high quality; and (5) providing an inexpensive, and simple process for preparing the aforementioned organic monomolecular film or lamination of monomolecular films having polyacetylenic or polydiacetylenic bonds.

BRIEF DESCRIPTION OF THE DRAWINGS

This invention may be better understood and its numerous objects and advantages will become apparent to those skilled in the art by reference to the accompanying drawings as follows:

FIGS. 8a, 8b, 8c, 8d and 8e show an example of the process of this invention, in which 13-DAS is used as a chemical adsorbent, and a catalyst is used to form a monomolecular film having trans-type polyacethylene bonds, and in which the surface of the film is further irradiated with a high energy beam to obtain a monomolecular film having polyacenic bonds.

DESCRIPTION OF THE PREFERRED EMBODIMENTS

Figure 1A:
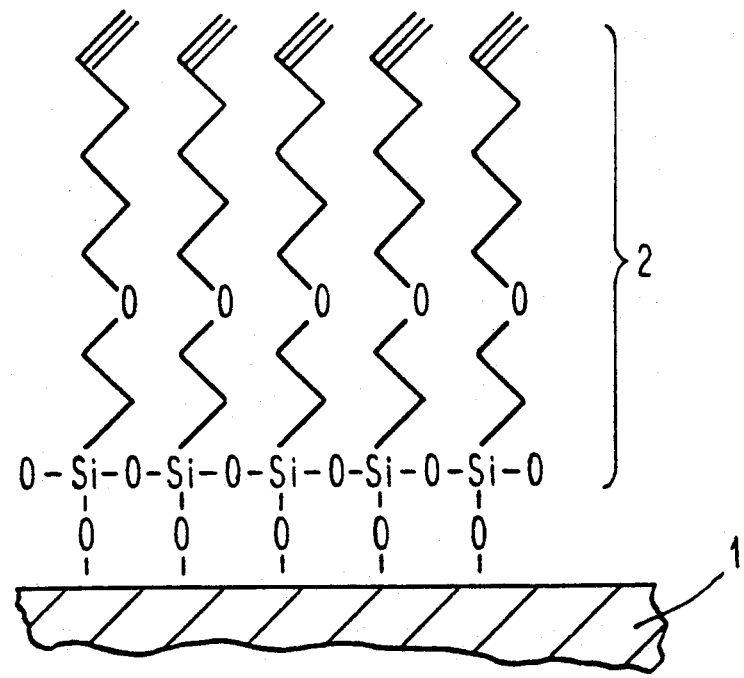
FIGS. 1a, 1b and 1c show an example of the process of this invention, in which 6-AOS is used as a chemical adsorbent, and a base plate to which the adsorbent has been bound is irradiated with a high energy beam, resulting in a monomolecular film having trans-type polyacetylenic bonds.

A chemical adsorbent used in the process for preparing an organic monomolecular film of this invention, having at least one triple bond, and a —SiCl group at one molecular end, is for example a hydrocarbon derivative represented by the following formula I:

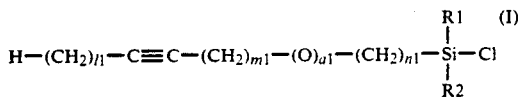

wherein R1 and R2 are each independently H, an alkyl or alkoxyl group having 1 to 4 carbon atoms, or halogen; l1, m1 and n1 are 0 or larger integers; the sum of l1, m1 and n1 is from 5 to 25; and a1 is 0 or 1.

Examples of the chemical adsorbent represented by the above-described formula I are illustrated below:

$CH \equiv C-(CH_2)_4-O-(CH_2)_2-SiCl_3$, and $CH_3-(CH_2)_8-C\equiv C-(CH_2)_3-O-(CH_2)_3-SiCl_3$ A chemical adsorbent that has a —SiH group or a —CH=CH₂ group at the other molecular end can be preferably used for preparing a lamination of monomolecular films that will be discussed below. This type of the chemical adsorbent is for example a hydrocarbon derivative presented by the following formula II:

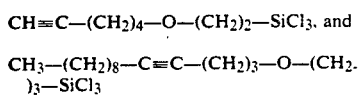

wherein said X¹ is

(R5 and R6 are each independently H, an alkyl group having 1 to 4 carbon atoms), or CH₂=CH—; R3 and R4 are each independently H, an alkyl or alkoxy group having 1 to 4 carbon atoms, or halogen; l2, m2 and n2 are 0 or larger integers; the sum of l2, m2 and n2 is from 5 to 25; and a2 is 0 or 1.

Examples of the chemical adsorbent represented by the above-described formula II are illustrated below:

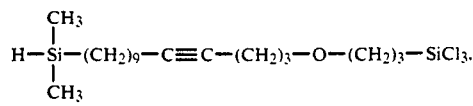

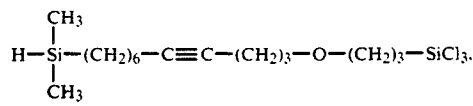

and

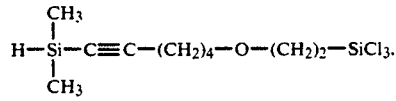

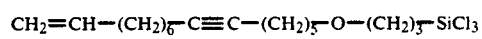

A chemical adsorbent used in another process for preparing an organic monomolecular film of this invention, having a diacetylene group, and a —SiCl group at one molecular end, is for example represented by the following formula III:

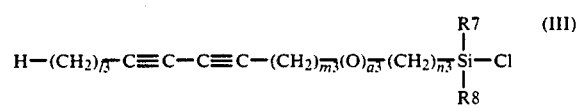

wherein R7 and R8 are each independently H, an alkyl or alkoxyl group having 1 to 4 carbon atoms, or halogen; l3, m3 and n3 are 0 or larger integers; the sum of l3, m3 and n3 is from 5 to 25; and a3 is 0 or 1.

Examples of the chemical adsorbent represented by the above-described formula III are illustrated below:

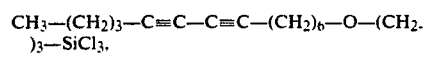

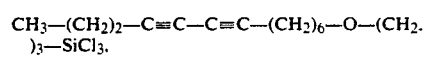

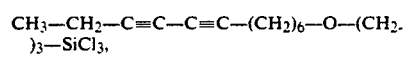

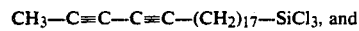

and

A chemical adsorbent that has a —SiH group or a —CH=H₂ group at the other molecular end can be preferably used for preparing a lamination of monomolecular films that will be discussed below. This type of the chemical adsorbent is for example represented by the following formula IV:

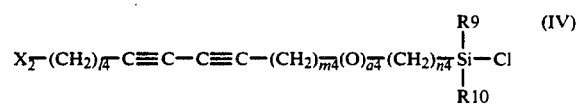

wherein said X² is

(R11 and R12 are each independently H, an alkyl group having 1 to 4 carbon atoms), or $CH_2=CH-$; R9 and R10 are each independently H, an alkyl or alkoxy group having 1 to 4 carbon atoms, or halogen; 4, m4 and n4 are 0 or larger integers; the sum of 4, m4 and n4 is from 5 to 25; and a4 is 0 or 1.

Examples of the chemical adsorbent represented by the above-described formula VI are illustrated below:

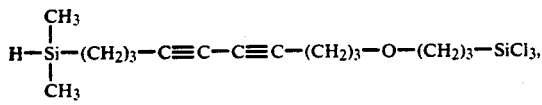

and

The organic monomolecular films prepared by the process of this invention have different molecular linkages, which depends on the chemical adsorbents and polymerization techniques used for the preparation. Table 1 illustrates examples of chemical adsorbents, polymerization techniques, and the types of the resulting monomolecular films.

TABLE 1

| Chemical Adsorbent | Polymerization Technique | Monomolecular Film |
|---|---|---|
| Compound having an acetylene group | High energy beam | Polyacetylene type (trans-type) |
| Compound having an acetylene group | Catalyst | Polyacetylene type (cis- or trans-type) |
| Compound having a diacetylene group | Low energy beam | Polydiacetylene type (mainly, 1,4-type) |
| Compound having a diacetylene group | Catalyst | cis-Polyacetylene type trans-Polyacetylene type $\xrightarrow{(a)}$ Polyacene type |
| Compound having a diacetylene group | High energy beam | Polyacetylene type (randam type[b]) Polydiacetylene type (1,2-type) |

[a] Further irradiation of high energy beam
[b] A mixture of cis-type and trans-type The following illustrates an example of the process of this invention by the use a chemical absorbent having an acetylene group, and a $-SiCl$ group at one molecular end, for example, the compound represented by the formula I.

A base plate having a functional group such as hydroxyl group, amino group, carboxyl group, and the like on its surface (i.e., a base plate having a hydrophilic surface) is first provided. For example, a silicon base plate having an oxidized film formed on its surface is preferably used. The oxidized film is formed by the treatment of the base plate with an oxidizing agent, or formed by autogenous oxidation. Next, the base plate is immersed in a solution of a chemical adsorbent in a non-aqueous organic solvent. The organic solvents which can be used include n-hexane, carbon tetrachloride, and the like, and mixtures thereof. The concentration of the chemical adsorbent may be varied depending on the kinds of base plate and its surface area, and is usually from $1.0 \times 10^{-3}$ to $4.0 \times 10^{-3}$ mole/L. By this immersion procedure, the $-Si-Cl$ group that is present in the chemical adsorbent reacts with a $-OH$ group that is present on the base plate, so that the chemical adsorbent can be bound chemically to the surface of the base plate. When the chemical adsorbent having $-SiCl_3$ is used, the monomolecular film shown in FIG. 1a is formed by the immersion procedure described above.

Then, the resulting monomolecular film 2 is irradiated with a high energy beam under an inert atmosphere to polymerize the chemical adsorbent at the triple bond, thereby forming a conjugated polymer having a polyacetylenic bond 3 (mainly, a trans-type polyacetylenic bond is formed). The high energy beam includes for example X-rays, an electron beam, gamma rays, an ion beam, etc.

For preparing a lamination of monomolecular films, a chemical adsorbent represented by the formula II is preferably used. For example, first monomolecular 2 is formed on the base plate 1 as shown in FIG. 1a by adsorbing the first chemical adsorbent of formula II ($X^1=H(CH_3)_2Si-$). The first monomolecular film is irradiated with a high energy polymerize the chemical adsorbent at the acetylene group, thereby forming a polyacetylenic bonds (FIG. 1c). Then, the first monomolecular film is treated with an alkaline to convert the $-SiH$ group at the molecular end into a $-SiOH$ group. Then, the base plate having the first monomolecular film is immersed into a solution of a second chemical adsorbent (which can be the same as or different from the first chemical adsorbent) to form a second monomolecular film. The resulting lamination of the first and second monomolecular films are irradiated with a high energy beam to polymerize the second adsorbent at the acetylene group, thereby forming a polyacetylenic group. When a lamination is prepared, the second monomolecular film can be formed after the polymerization of the first monomolecular film as described above. Alternatively, a lamination composed of a non-polymerized films can be irradiated to form polyacetylenic bonds.

When a chemical adsorbent represented by the formula II wherein X is $-CHCH_2$ is used, the first monomolecular film is contacted with diborane solution followed by a solution containing alkali and $H_2O_2$ to convert the $-CH=CH_2$ group at the molecular end into a $-CH_2-CH_2-OH$ group. The same conversation reaction is conducted by irradiating the first monomolecular film with X-rays, an electron beam, gamma rays, etc., under an atmosphere containing oxygen instead of contacting with diborane solution. Also, in the case of irradiating the first monomolecular film with X-rays, an electron beam, gamma rays, etc., under nitrogen atmosphere, the $-CH=CH_2$ group is converted into a $-NH_2$ group. Then, the base plate having the first monomolecular film is immersed into a solution of the second chemical adsorbent by the same procedure as described above to form the second monomolecular film. The second monomolecular film is irradiated with a high energy beam to polymerize the chemical adsorbent, thereby forming a monomolecular film having polyacetylenic bonds.

If a chemical adsorbent represented by the formula II is also used as the second chemical adsorbent in the process for preparing a lamination of monomolecular films described above, and the same procedure is repeated consecutively, a lamination of monomolecular films having three, four, or more layers can be obtained.

As a chemical adsorbent, a compound having an oxygen atom in its principal chain (i.e., a1, a2, a3, or a4 is one in FIGS. 1, 2, 3, or 4, respectively is preferably used. When the chemical adsorbent is adsorbed on a base plate, the degree of the molecule is high, so that the polymerization produce and not inhibited by any twisting of the molecule. Thus, the degree of polymerization will be high. This type of chemical adsorbent is particularly preferable when the rubbing process described below is performed.

The following two techniques can be used for providing a monomolecular film with a polymerization orientation, the first technique comprising inactivating triple bonds that are present in a certain portion whereas the second technique comprises rubbing the monomolecular film.

Figure 1B:
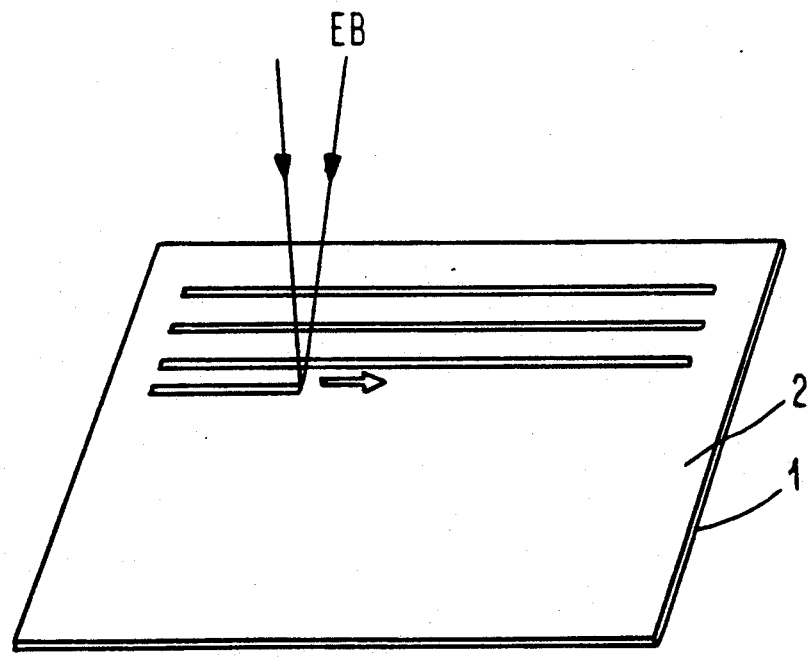
Figure 1C:
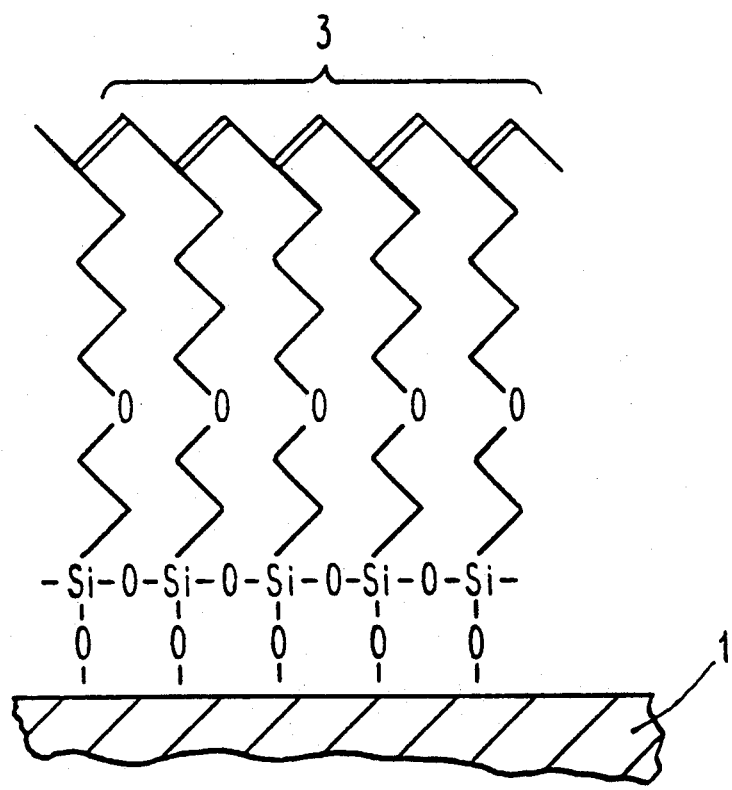

According to the first technique, the monomolecular film formed on the base plate as described above is exposed to an electron beam or X-rays, or by carrying out a writing onto the surface of the film by the use of a Scanning Tunneling Microscope (STM), at a given interval in a certain direction to inactivate the triple bond present in the exposed portion (See, FIG. 1b). The interval is usually from 1 to 0.01 μm. The exposure is conducted under an inactive or active atmosphere. When the monomolecular film is exposed under an inactive atmosphere such as nitrogen atmosphere, the triple bond present in the exposed portion is polymerized. On the other hand, when the monomolecular film is exposed under an active atmosphere, a triple bond cleavage will occur, and then other atoms will be bound to the cleavage portion. For example, when it is exposed under oxygen atmosphere, an oxygen atom will be introduced into the monomolecular film structure. Because the triple bond present in the exposed portion of the monomolecular film disappears (hereinafter referred to "inactivated"), the exposed portion will cease to be further polymerized. Then, the exposed monomolecular film is irradiated with a high energy beam to polymerize the remaining chemical adsorbent having a triple bond, thereby forming a trans-type polyacetylenic bond as shown in FIG. 1c. As the triple bond of the monomolecular film is inactivated in a stripe pattern, the polymerization direction is regulated, i.e., the polymerization produces linearly in a certain direction. Therefore, a monomolecular film having a highly oriented polyacetylenic bond can be obtained.

The second technique comprises first forming a monomolecular film on a base plate by the same procedure as used in the first technique. Next, the surface of the monomolecular film is rubbed with e.g., non-woven fibers such as a piece of felt, in a certain direction to orient the chemical adsorbent molecules. When a chemical adsorbent having an oxygen atom in its principal chain is used, the degree of freedom of the molecules is high, so that the rubbing procedure may readily be performed. Then, the rubbed monomolecular film is irradiated with a high energy beam under an inert atmosphere such as nitrogen to polymerize the chemical adsorbent at the triple bond that is present in the monomolecular film, thereby forming polyacetylenic bonds in trans configuration. Because the chemical adsorbent molecules are oriented by rubbing, the polymerization direction is regulated, i.e., the polymerization produces linearly in a certain direction. Therefore, a monomolecular film having a highly oriented polyacetylenic bond can be obtained.

As is described above, a desired highly oriented monomolecular film can be obtained by either the first technique or the second technique, using a suitable chemical adsorbent.

A highly oriented monomolecular film can also be formed by using a chemical adsorbent having a diacetylene group, and a —SiCl group at one molecular end, for example a compound represented by the formula III or IV described above, instead of a chemical adsorbent having an acetylene group by basically the same procedure as described above.

When the monomolecular film formed by the chemical adsorbent having a diacetylene group is irradiated with a high energy beam, a monomolecular film having random-type polyacetylenic bonds, i.e., a mixture of cis- and trans-type polyacetylenic bonds, will be formed. When a monomolecular film is made of chemical adsorbent molecules with relatively high density, a monomolecular film having 1,2-type polydiacetylenic bonds will be formed. This 1,2-type polydiacetylenic bond is formed by linking a carbon atom at the 1-position of a diacetylene group in a chemical adsorbent molecule to a carbon atom at the 2-position of a diacetylene group in an adjacent chemical adsorbent molecule.

On the other hand, when the monomolecular film formed by the chemical adsorbent having a diacetylene group is irradiated with a low energy beam instead of a high energy beam, polydiacetylenic bonds will be formed. An ultraviolet radiation can preferably be used as a low energy beam. When a monomolecular film made of chemical adsorbent molecules with a relatively low density, a monomolecular film having a 1,4-type polyacetylenic bond will be obtained. This 1,4-type polydiacetylenic bond is formed by linking a carbon atom at the 1-position of a diacetylene group in a chemical adsorbent molecule to a carbon atom at 4-position of a diacetylene group in an adjacent chemical adsorbent molecule. In order to adsorb the chemical adsorbent with low density on a base plate, a solution of the chemical adsorbent in an organic solvent in a concentration of from $1 \times 10^{-2}$ to $1 \times 10^{-4}$ mol/L is preferably used. The resulting monomolecular film having 1,4-diacetylene bonds is useful for an optical recording medium.

Also, a metal compound can be used as a catalyst for polymerizing the monomolecular film other than the aforementioned high and low energy beams. The metal compounds include those containing Mo, W, Nb or Ta, especially those containing a halogen being preferred. These compounds include $MoCl_5$, $WCl_6$, $NbCl_5$, $TaCl_5$, $Mo(CO)_5$, $W(CO)_6$, $Nb(CO)_5$, $Ta(CO)_5$, and like. A co-catalyst can be used in combination with the catalyst. The co-catalyst enhances the catalytic ability, and includes $(C_6H_5)_3Bi$, $(C_6H_5)_4Sn$ or the like.

The following describes a polymerization technique by the use of metal compound. A monomolecular film is formed by adsorbing a chemical adsorbent having an acetylene group or a diacetylene group on a base plate by the procedure described above. The monomolecular film is then immersed into a solution of the metal compound in an organic solvent. A non-aqueous organic solvent is usually used as an organic solvent. By this immersion procedure, the chemical adsorbent is polymerized at the acetylene group or diacetylene group to form a monomolecular film having a trans-type polyacetylenic bonds. Cis-type polyacetylenic bonds can also be formed when a specific organic solvent is used in combination with a suitable catalyst. The organic solvent that is used is a solvent having oxygen atom is its own molecule. The solvent includes tetrahydrofuran, dioxane, anisole, and the like. FIGS. 6b and 7b show monomolecular films having cis.type polyacetylenic bonds.

Furthermore, a monomolecular film having polyacenic bonds shown in FIG. 8e can be prepared by the following procedure. A monomolecular film having a trans-type polyacetylenic bond is formed from the chemical adsorbent having a diacetylene group by the same procedure as described above by the use of a metal compound as a catalyst. Then, the whole surface of the catalyst-treated monomolecular film is irradiated with a high energy beam to produce further polymerization, thereby forming polyacenic bonds.

When triple bonds are inactivated by the irradiation of electron beams etc., or the chemical adsorbent molecules are oriented by the rubbing mentioned above, the inactivation or rubbing process is performed before the irradiation by the high energy beam. In other words, the inactivation or rubbing process is performed after the formation of the monomolecular film on the base plate using the chemical adsorbent, or after the immersion of the base to form trans-type diacetylene bonds. The resulting monomolecular film having a polyacenic bond is particularly useful as a molecular wire.

Consequently, various organic monomolecular films having different types of linkages are obtained by the procedures described above. The thickness of the resulting monomolecular films is from 10 to 100Å. Optionally, a lamination of organic monomolecular films can be prepared by laminating another monomolecular film on the surface of the resulting monomolecular film. A monomolecular film obtained by the procedure comprising an inactivation process of an acetylene or diacetylene group, or rubbing process of a monomolecular film is highly oriented. The monomolecular film has relatively higher molecular weight, e.g., at least several hundreds. When chemical adsorbent molecules polymerizes, a longer conjugated system is formed because the polymerization is not interrupted by a molecular twisting. Therefore, the resulting monomolecular film having polyacetylene, polydiacetylene or polyacenic bonds can be used for optical recording medium, etc. Also, because the monomolecular polymer film has a longer conjugated system, so that the polymer film rarely acts with oxygen. Therefore, the film is stable under an oxygen atmosphere, and its quality is maintained for a long period of time. As is described above, according to the process of this invention, a polyacetylene-, polydiacetylene-, or polyacene-type monomolecular film with high stability, high electric conductivity and excellent nonlinear optical effect can be prepared.

EXAMPLES

The following illustrates examples of this invention in detail.

Example 1

A semiconductive silicon base plate/having 3 inch diameter, the surface of which, has been oxidized to form $SiO_2$ was provided.

A chemical adsorbent represented by the following formula was used in this example:

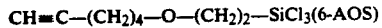
CH≡C—$(CH_2)_4$—O—$(CH_2)_2$—$SiCl_3$(6-AOS)

This chemical adsorbent has an acetylene group, and a —SiCl group at one molecular end. The chemical adsorbent was dissolved into a mixed solvent containing 85 wt % of n-hexane, 8 wt % of carbon tetrachloride, and 7 wt % of chloroform in a concentration of $1 \times 10^{-3}$ mol/L. The aforementioned silicon base plate was immersed into this solution for 30 minutes under a dry nitrogen atmosphere. By this immersion procedure, as shown in FIG. 1a, the trichlorosilyl group that was present at the end of the chemical adsorbent was bound to the —OH group on the base plate, and the elimination of hydrogen chloride occurred. Thus, the chemical adsorbent was bound covalently to the base plate by a —Si—O— linkage to form a first monomolecular film 2. The presence of the first monomolecular film composed of the residue of the chemical adsorbent represented by the following formula on the base plate was identified by FTIR analysis. (See, FIG. 1c):

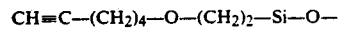
CH≡C—$(CH_2)_4$—O—$(CH_2)_2$—Si—O—

Then, the whole surface of the monomolecular film was irradiated with an electron beam (5 to 10 mJ/cm$^2$) under a helium atmosphere to polymerize the chemical adsorbent at the acetylene group, thereby forming a monomolecular film having trans-type polyacetylenic bonds 3 (See, FIG. 1c). The same result was obtained with X-rays or a gamma beam. The presence of the trans-type polyacetylenic bonds was identified by the FTIR analysis.

Example 2

A semiconductive silicon base plate/having a 3 inch diameter, the surface of which, has been oxidized to form $SiO_2$ was provided.

A chemical adsorbent represented by the following formula was used in this example:

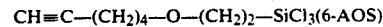
CH≡C—$(CH_2)_4$—O—$(CH_2)_2$—$SiCl_3$(6-AOS)

This chemical adsorbent has an acetylene group, and a —SiCl group at one molecular end. The chemical adsorbent was dissolved into a mixed solvent containing 85 wt % of n-hexane, 8 wt % of carbon tetrachloride, and 7 wt % of chloroform in a concentration of $1 \times 10^{-3}$ mol/L. The aforementioned silicon base plate was immersed into this solution for 30 minutes under a dry nitrogen atmosphere. By this immersion procedure, as shown in FIG. 1a, trichlorosilyl group that was present at the end of the chemical adsorbent was bound to the —OH group on the base plate, and the elimination of hydrogen chloride occurred. Thus, the chemical adsorbent was bound covalently to the base plate by a —Si—O— linkage to form a first monomolecular film 2. The presence of the first monomolecular film composed of the residue of the chemical adsorbent represented by the following formula on the base plate was identified by FTIR analysis. (See, FIG. 1c):

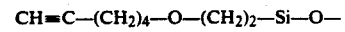
CH≡C—$(CH_2)_4$—O—$(CH_2)_2$—Si—O—

Next, the monomolecular film was exposed to an electron beam at a given interval in a certain direction under a helium atmosphere to inactivate the acetylene groups, that are present in the exposed portion as shown in FIG. 1b. Then, the whole surface of the monomolecular film was irradiated with an electron beam (5 to 10 mJ/cm²) under a helium atmosphere to polymerize the chemical adsorbent at the acetylene group, thereby forming a monomolecular film having trans-type polyacetylenic bonds 3 (See, FIG. 1c). The same result was obtained with X-rays or a gamma beam. The presence of the trans-type polyacetylenic bonds was identified by FTIR analysis. As is described above, a monomolecular polymer film having polyacetylenic bonds with higher orientation was obtained.

Example 3

A monomolecular polymer film having transtype polyacetylenic bonds with higher orientation was obtained by the same procedure as in Example 2 except that a chemical adsorbent represented by the following formula was used:

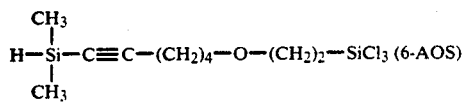

H—Si(CH₃)₂—C≡C—(CH₂)₄—O—(CH₂)₂—SiCl₃ (6-AOS)

Figure 2A:
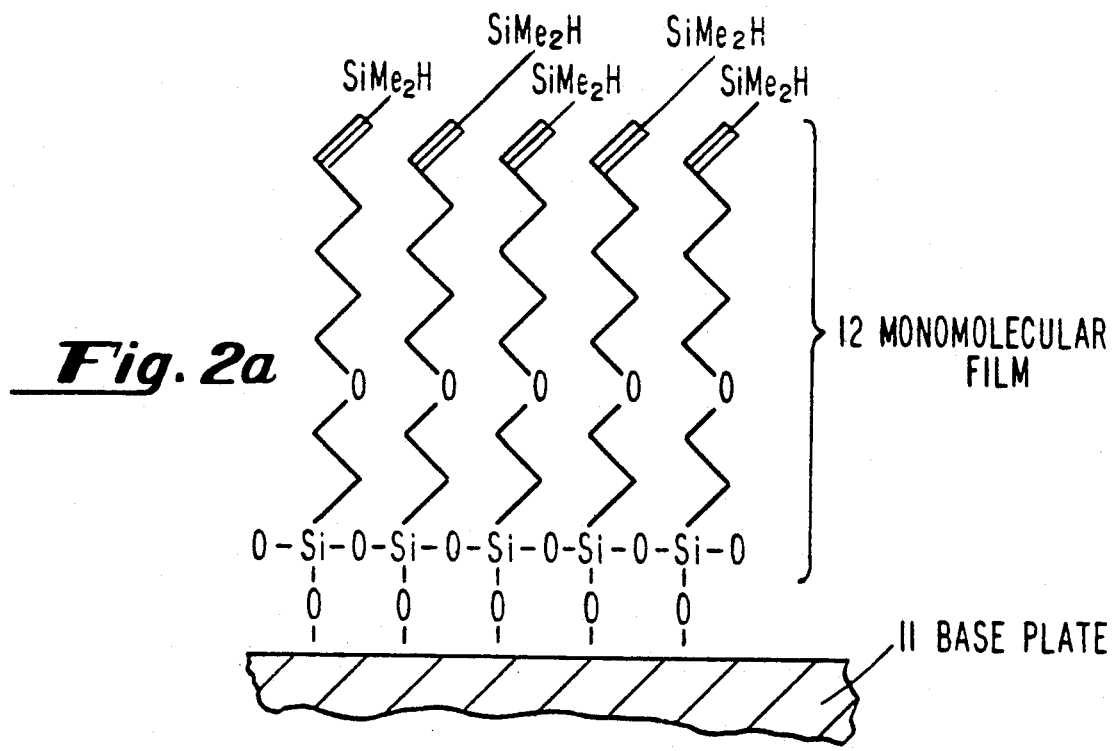
FIGS. 2a, and 2b show an example of the process of this invention, in which DMS-6-AOS is used as a chemical adsorbent, and a base plate to which the adsorbent has been bound is irradiated with a high energy beam, resulting in a monomolecular film having trans-type polyacetylenic bonds.
Figure 2B:
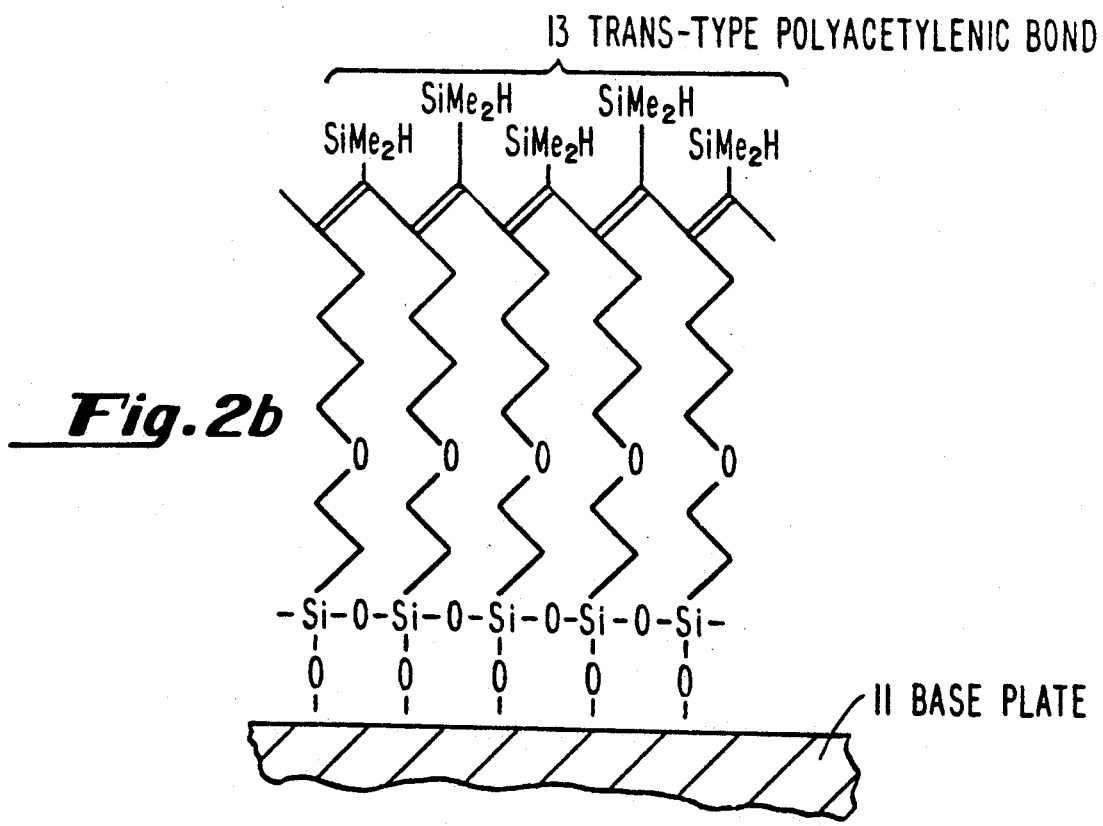

The procedure of this example is shown in FIGS. 2a and 2b.

Example 4

(A) A first monomolecular film was formed on a base plate by the same procedure as in Example 1, using 6-AOS as a chemical adsorbent. The base plate having the first monomolecular film formed on its surface was immersed into NaOH aqueous solution of pH12 for 10 minutes to convert the H(CH₃)₂Si— group into a HO(CH₃)₂Si— group. Then, the base plate was immersed into the same kind of chemical adsorbent solution by the same procedure as used for the formation of the first monomolecular film. Thus the second monomolecular film was formed. The resulting lamination of monomolecular films was exposed to an electron beam at a given interval in a certain direction to inactivate the acetylene groups that were present in the exposed portion. Then, by the same procedure as in Example 2, the whole surface of the laminated monomolecular film was irradiated with an electron beam (5 to 10 mJ/cm²) under a helium atmosphere to polymerize the remaining chemical adsorbent molecules having the acetylene groups. As is described above, a polymer monomolecular film having polyacetylenic bonds with higher orientation was obtained.

(B) The first monomolecular film was formed by the same procedure as in item A except that a chemical adsorbent represented by the following formula was used:

CH₂=CH—C≡C—(CH₂)₄—O—(CH₂)₂—SiC₃

The base plate having the first monomolecular film formed on its surface was immersed into a solution of diborane in THF (1 mol/L) at room temperature, followed by 30% aqueous H₂O₂ solution containing 0.1 mol/L of NaOH to convert the —CH=CH₂ group into a —CH₂CH₂OH group. The same kind of chemical adsorbent was adsorbed on the first monomolecular film to form the second monomolecular film. Then by the same procedure as in item A, a monomolecular film having trans-type polyacetylenic bonds was obtained.

Example 5

A chemical adsorbent represented by the following formula was adsorbed on a base plate 31 by the same procedure as in Example 2 (See, FIG. 3a):

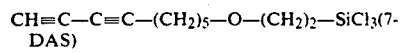

CH≡C—C≡C—(CH₂)₅—O—(CH₂)₂—SiCl₃(7-DAS)

Figure 3A:
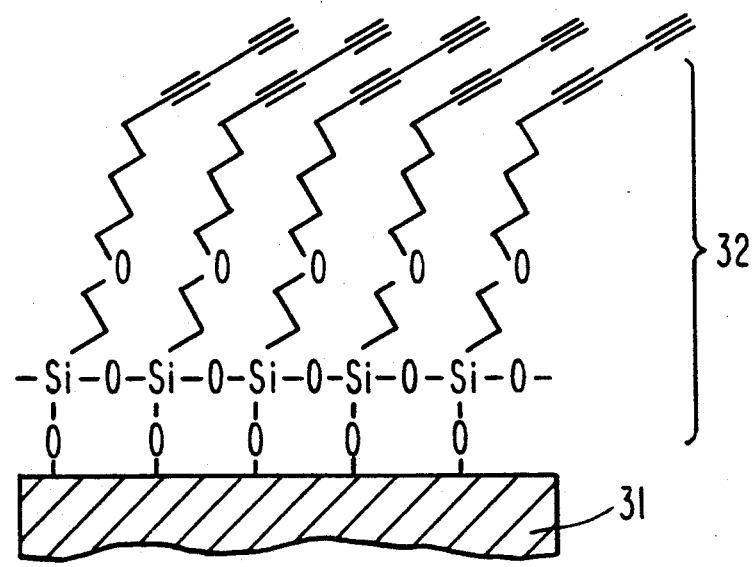
FIGS. 3a, 3b and 3c show an example of the process of this invention, in which 7-DAS is used as a chemical adsorbent and a base plate to which the adsorbent has been bound is irradiated with a high energy beam, resulting in a monomolecular film having transtype polyacetylenic bonds.
Figure 3B:
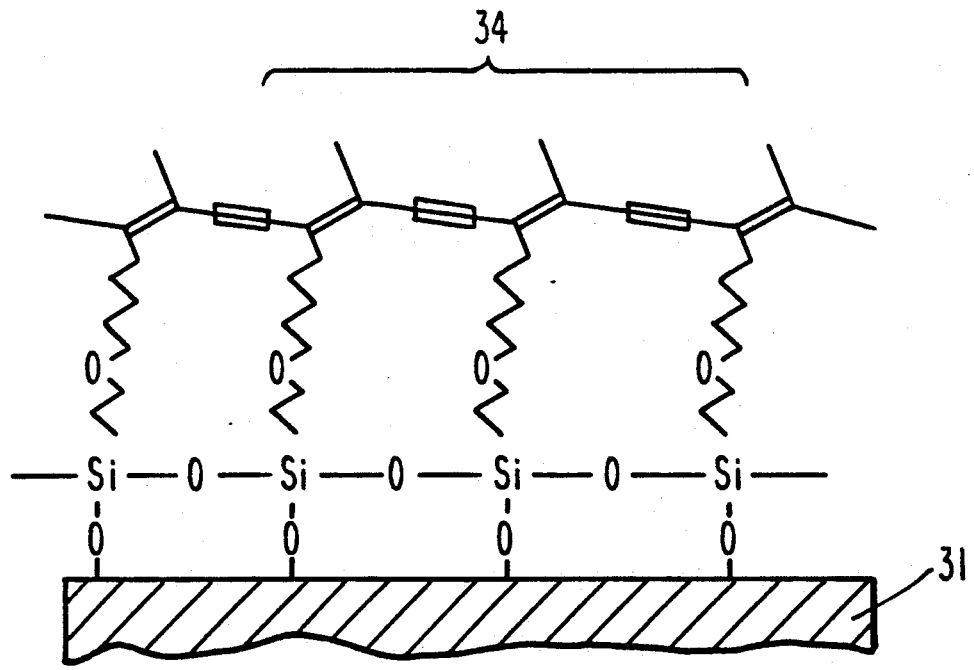

After the monomolecular film was exposed to an electron beam at a given interval in a certain direction as described in Example 2 to inactivate the diacetylene groups present in the exposed portion, and then the whole surface of the monomolecular film was irradiated with ultraviolet rays (5 to 10 mJ/cm²) under an inert atmosphere, thereby forming a highly oriented monomolecular film having 1,4-type polydiacetylenic bonds 34 as shown in FIG. 3b.

Example 6

Figure 3C:
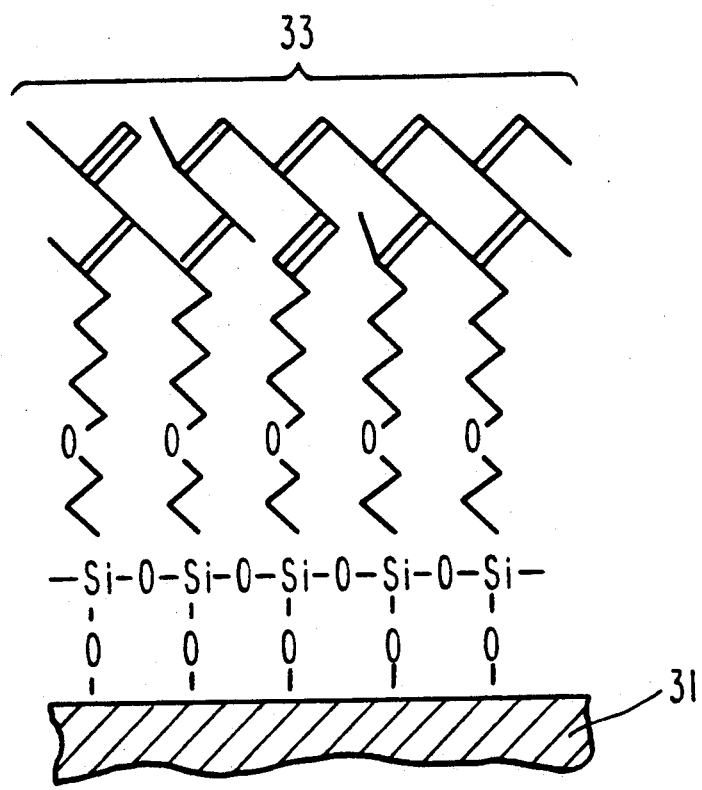

The same procedure as in Example 5 was repeated except that X-rays, an electron beam, or a gamma beam (5 mJ/m²) was irradiated instead of ultraviolet rays to form a highly oriented monomolecular film having polyacetylenic bonds, as shown in FIG. 3c.

Example 7

(A) The first and second monomolecular films were formed on a base plate by the same procedure as in Example 4A except that a chemical adsorbent represented by the following formula was used:

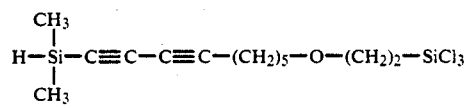

H—Si(CH₃)₂—C≡C—C≡C—(CH₂)₅—O—(CH₂)₂—SiCl₃

The lamination of monomolecular films was exposed to an electron beam at a given interval in a certain direction as described in Example 2 to inactivate the diacetylene groups present in the exposed portion. Then the whole surface of the monomolecular film was irradiated with ultraviolet rays (5 to 10 mJ/cm²) under an inert atmosphere, thereby forming a highly oriented monomolecular film having 1,4-type polydiacetylenic bonds 34, as shown in FIG. 3b.

(B) The first and second monomolecular films were formed on a base plate by the same procedure as in Example 4B except that a chemical adsorbent represented by the following formula was used:

CH₂=CH—C≡C—C≡C—(CH₂)₅—O—(CH₂)₂—SiCl₃

The lamination of monomolecular films was exposed to an electron beam at a given interval in a certain direction as described in Example 2 to inactivate the diacetylene groups present in the exposed portion. Then the whole surface of the monomolecular film was irradiated with ultraviolet rays (5 to 10 mJ/cm²) under an inert atmosphere, thereby forming a highly oriented monomolecular film having 1,4-type polydiacetylenic bonds 34, as shown in FIG. 3b.

Example 8

The same procedure as in Example 7 was repeated except that X-rays, an electron beam, or a gamma beam (5 mJ/m²) was irradiated instead of ultraviolet rays to form a highly oriented laminated monomolecular film having poly acetylene bonds.

Examples 9-15

The procedures of Examples 2-8 were repeated except that the monomolecular film was rubbed in a certain direction instead of exposing it into an electron beam at a given interval in a certain direction to inactivate the acetylene or diacetylene groups that were present in the exposed portion. In Examples 11, 14, and 15, after the first monomolecular film was formed on the base plate, the surface of the film was rubbed, then the second monomolecular film was formed, rubbed, and irradiated with a high energy beam (i.e., an electron beam, X-rays, or a gamma beam) or a low energy beam (i.e., ultraviolet rays).

Example 16

A semiconductive silicon base plate/having a 3 inch diameter, the surface of which, has been oxidized to form $SiO_2$ was provided.

A chemical adsorbent represented by the following formula was used in this example:

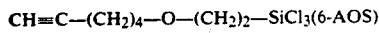

$CH \equiv C-(CH_2)_4-O-(CH_2)_2-SiCl_3$ (6-AOS)

This chemical adsorbent has an acetylene group, and a —SiCl group at one molecular end. The chemical adsorbent was dissolved into a mixed solvent containing 85 wt % of n-hexane, 8 wt % of carbon tetrachloride, and 7 wt % of chloroform in a concentration of $1 \times 10^{-3}$ mol/L. The aforementioned silicon base plate was immersed into this solution for 30 minutes under a dry nitrogen atmosphere. By this immersion procedure, as shown in FIG. 1a, the trichlorosilyl group that was present at the end of the chemical adsorbent was bound to the —OH group on the base plate, and the elimination of hydrogen chloride occurred Thus, the chemical adsorbent was bound covalently to the base plate by a —Si—O— linkage to form a first monomolecular film 2. The presence of the first monomolecular film composed of the residue of the chemical adsorbent represented by the following formula on the base plate was identified by FTIR analysis. (See, FIG. 1c):

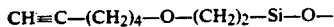

$CH \equiv C-(CH_2)_4-O-(CH_2)_2-Si-O-$

Figure 4A:
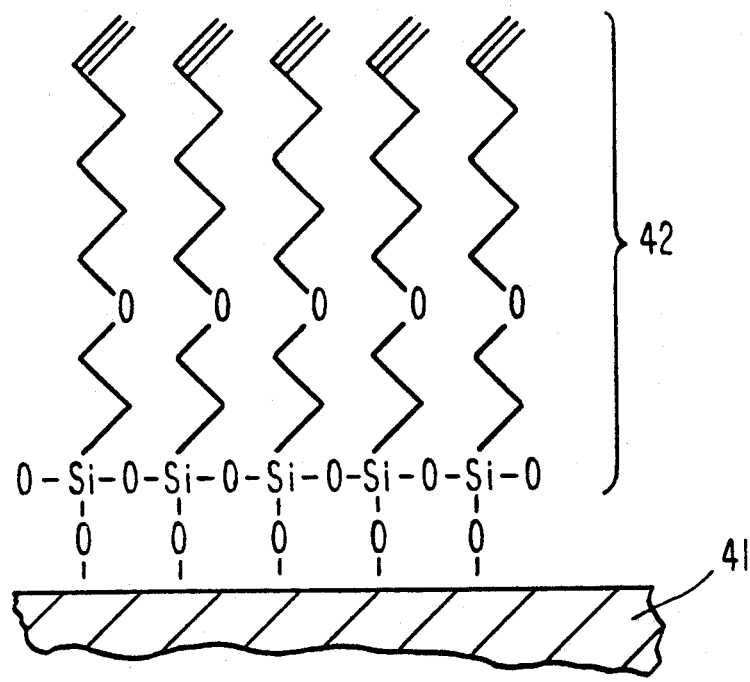
FIGS. 4a, 4b and 4c show an example of the process of this invention, in which 6-AOS is used as a chemical adsorbent and a catalyst is used to form a monomolecular film having trans-type polyacetylenic bonds.

Separately, a catalyst solution was prepared by dissolving $MoCl_5$ into toluene in a concentration of $2 \times 10^{-2}$ mol/L. The base plate having the monomolecular film formed as described above was immersed into the catalyst solution at 25° C. for 10 minutes to polymerize the chemical adsorbent at the acetylene group, thereby forming a monomolecular film having trans-type polyacetylenic bonds as shown in FIG. 4.

When $Mo(Co)_6$ or $W(Co)_6$ was used as a catalyst, and the base plate having the non-polymerized monomolecular film was immersed in a chloroform solution containing the catalyst with the simultaneous ultraviolet radiation, a red-brown polymerized monomolecular film was obtained.

This polymer monomolecular film has polyacetylene bonds, and higher molecular weight compared with the above-mentioned film.

Example 17

A semiconductive silicon base plate having a 3 inch diameter, the surface of which, had been oxidized to form $SiO_2$ was provided.

A chemical adsorbent represented by the following formula was used in this example:

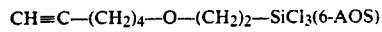

$CH \equiv C-(CH_2)_4-O-(CH_2)_2-SiCl_3$ (6-AOS)

This chemical adsorbent has an acetylene group, and a —SiCl group at one molecular end. The chemical adsorbent was dissolved into a mixed solvent containing 85 wt % of n-hexane, 8 wt % of carbon tetrachloride, and 7 wt % of chloroform in a concentration of $1 \times 10^{-3}$ mol/L. The aforementioned silicon base plate was immersed into this solution for 30 minutes under a dry nitrogen atmosphere. By this immersion procedure, as shown in FIG. 1a, the trichlorosilyl group that was present at the end of the chemical adsorbent was bound to the —OH group on the base plate, and the elimination of hydrogen chloride occurred Thus, the chemical adsorbent was bound covalently to the base plate by a —Si—O— linkage to form a first monomolecular film 2. The presence of the first monomolecular film composed of the residue of the chemical adsorbent represented by the following formula on the base plate was identified by FTIR analysis. (See, FIG. 1c):

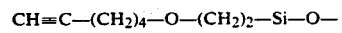

$CH \equiv C-(CH_2)_4-O-(CH_2)_2-Si-O-$

Figure 4B:
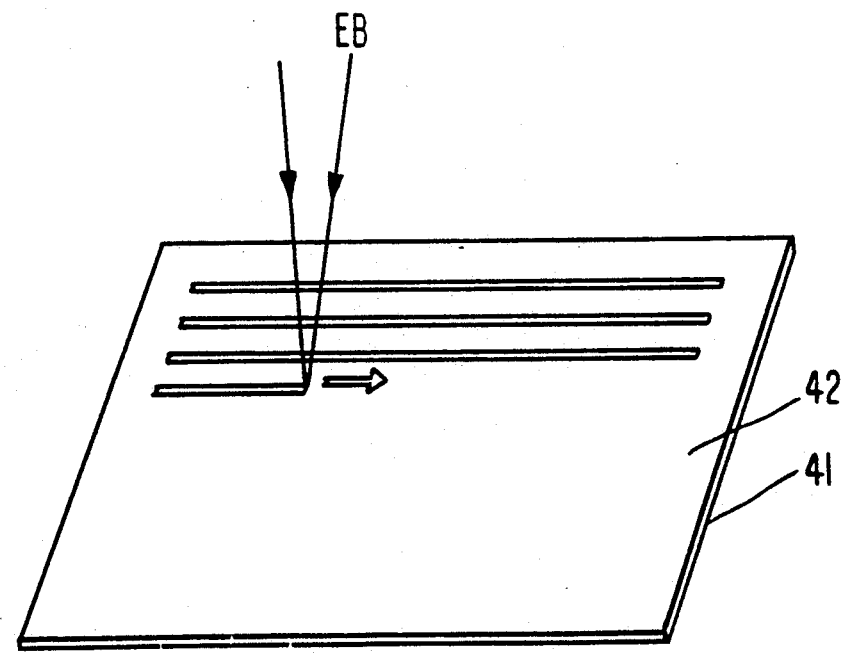
Figure 4C:
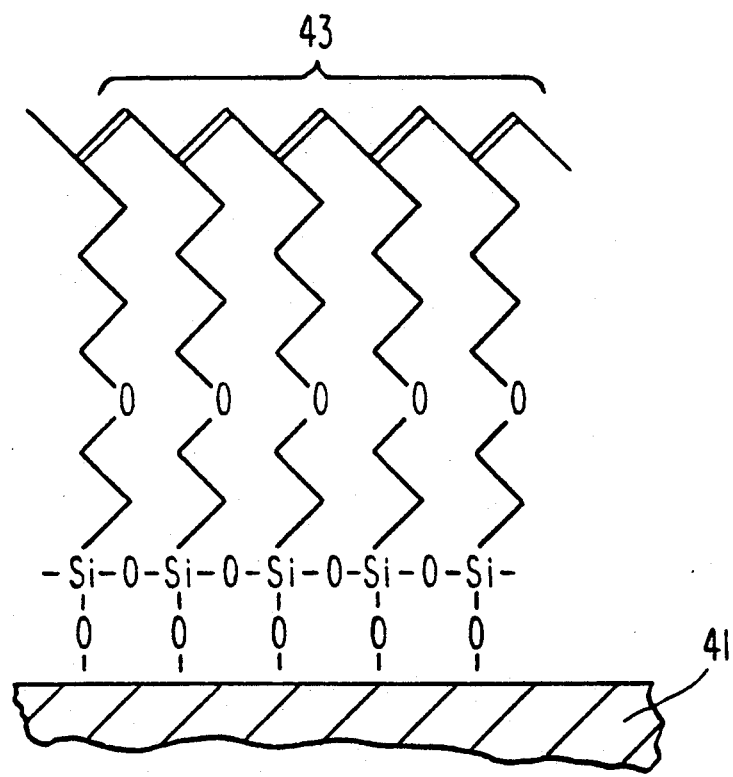

Then, as shown in FIG. 4b, the monomolecular film was exposed to an electron beam at a given interval in a certain direction to inactivate the acetylene groups that were present in the exposed portion. Separately, a catalyst solution was prepared by dissolving $MoCl_5$ into toluene in a concentration of $2 \times 10^{-2}$ mol/L. The base plate having the monomolecular film formed as described above was immersed into the catalyst solution at 25° C. for 10 minutes to polymerize the chemical adsorbent molecules at the remaining acetylene groups, thereby forming a highly oriented monomolecular film having trans-type poly acetylene bonds as shown in FIG. 4.

Example 18

A monomolecular film having trans-type polyacetylene bonds with a higher orientation was obtained by the same procedure as in Example 17 except that a chemical adsorbent represented by the following formula was used:

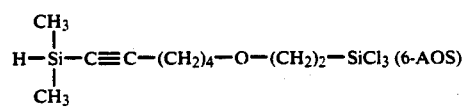

$$\begin{array}{c} CH_3 \\ | \\ H-Si-C\equiv C-(CH_2)_4-O-(CH_2)_2-SiCl_3 \text{ (6-AOS)} \\ | \\ CH_3 \end{array}$$

Figure 5A:
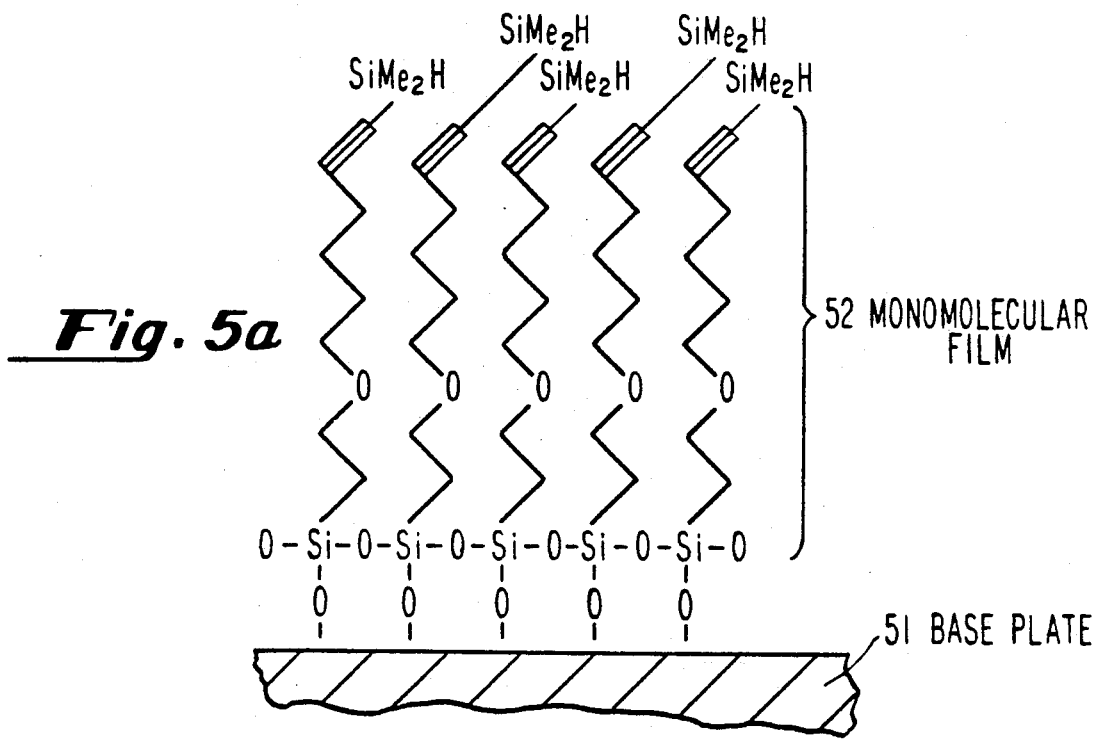
FIGS. 5a, and 5b show an example of the process of this invention, in which DMS-6-AOS is used as a chemical adsorbent and a catalyst is used to form a monomolecular film having trans-type polyacetylenic bonds.
Figure 5B:
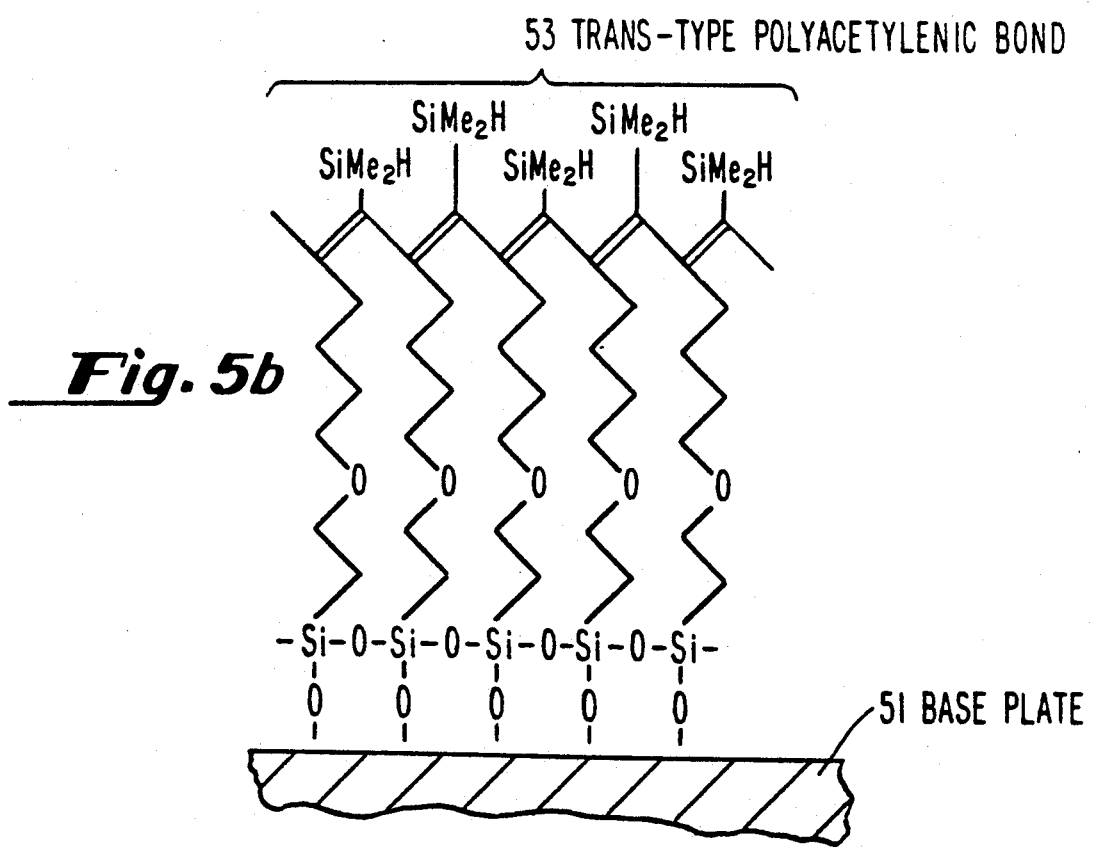

The procedure of this example is shown in FIGS. 5a and b.

Example 19

(A) A first monomolecular film was formed on a base plate by the same procedure as in Example 16, using a chemical adsorbent represented by the following formula:

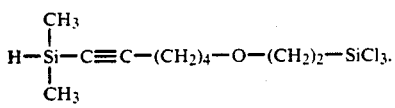

Then, the whole surface of the monomolecular film was irradiated with an electron beam (5 to 10 mJ/cm$^2$) under a helium atmosphere to polymerize the chemical adsorbent at the acetylene group, thereby forming a monomolecular film having trans-type polyacetylenic bonds 3 (See, FIG. 1c). The same result was obtained with X-rays or a gamma beam. The presence of the trans-type polyacetylenic bonds was identified by the FTIR analysis.

Separately, a catalyst solution was prepared by dissolving a mixture of WCl$_5$ (catalyst) and Bu$_4$Sn (co-catalyst) in the moler ratio of 1:1 into toluene in a concentration of $1 \times 10^{-2}$ mol/L. The base plate having the monomolecular film formed as described above was immersed into the catalyst solution for 10 minutes at 25° C. to polymerize the chemical adsorbent. Next, the base plate was immersed into NaOH aqueous solution of pH$_{12}$ for 10 minutes to convert the H(CH$_3$)$_2$Si— group into a HO(CH$_3$)$_2$Si— group. Then, the base plate was immersed in the same kind of chemical adsorbent solution by the same procedure as used for the formation of the first monomolecular film to form the second monomolecular film. The resulting lamination of monomolecular films was exposed to an electron beam at a given interval in a certain direction to inactivate the acetylene groups present in the exposed portion. Then, the base plate was immersed in the same kind of catalyst solution as mentioned above to polymerize the remaining chemical adsorbent having the acetylene group, thereby forming a highly oriented monomolecular film having a trans-type polyacetylenic bond.

(B) A lamination of monomolecular films was prepared by the similar procedure as in item A above. In this example, a chemical adsorbent represented by the following formula was used:

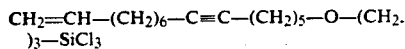

After the first monomolecular film was polymerized, the base plate was immersed into a solution of diborane in THF (1 mol/L) at room temperature, followed by an immersion in a 30% aqueous H$_2$O$_2$ solution containing 0.1 mol/L of NaOH to change the —CH=CH$_2$ group into a —CH$_2$CH$_2$OH group. The same chemical adsorbent was adsorbed on the first monomolecular film to form the second monomolecular film, and then by the same procedure was repeated as in item A. Thus, a monomolecular film having trans-type polyacetylenic bonds was obtained.

The laminations of monomolecular films obtained in A and B were both insoluble in an alcohol.

Example 20

Figure 6A:
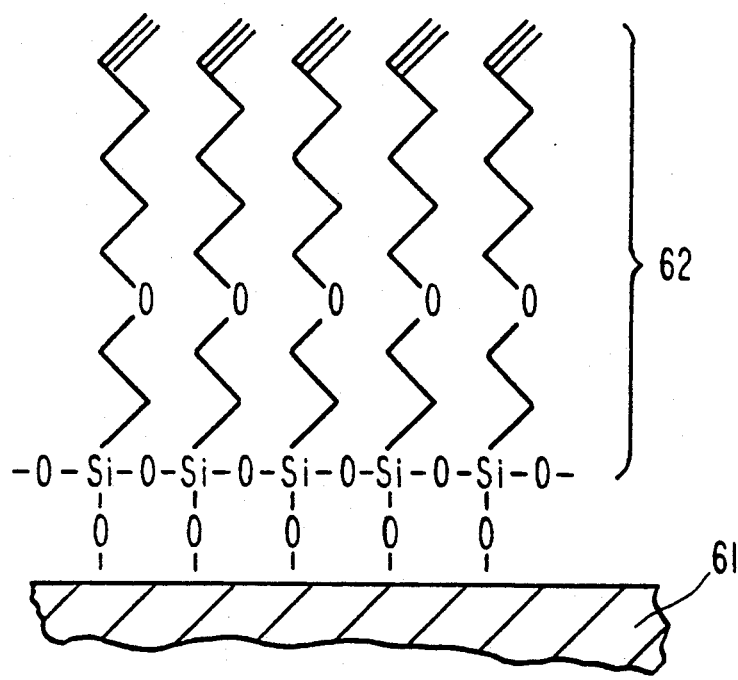
FIGS. 6a, and 6b show an example of the process of this invention, in which 6-AOS is used as a chemical adsorbent and a catalyst is used to form a monomolecular film having cis-type polyacetylenic bonds.
Figure 6B:
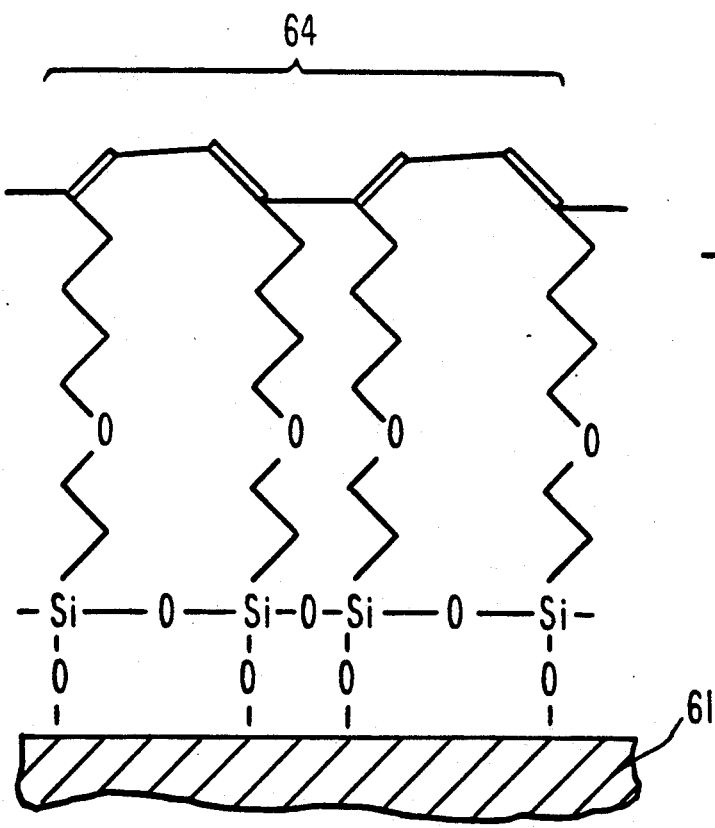

A monomolecular film was formed on a base plate 61 by the same procedure as in Example 17, using 6-AOS as a chemical adsorbent (See, FIG. 6a). The monomolecular film was exposed to an electron beam at a given interval in a certain direction to inactivate the acetylene group that was present in the exposed portion. Separately, a catalyst solution was prepared by dissolving MoCl$_6$ into anisole in a concentration of $2 \times 10^{-2}$ mol/L. The base plate having the monomolecular film formed as described above was immersed into the catalyst solution for 10 minutes at 25° C. to polymerize the remaining chemical adsorbent having the acetylene group, thereby forming a highly oriented monomolecular film having cis-type polyacetylenic bonds (See, FIG. 6b).

Example 21

Figure 7A:
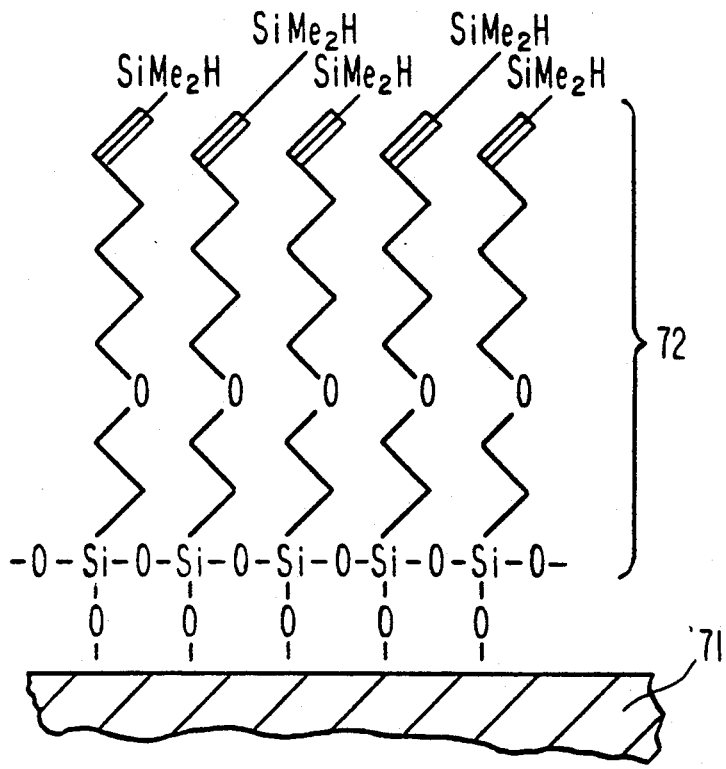
FIGS. 7a, and 7b show an example of the process of this invention, in which DMS-6-AOS is used as a chemical adsorbent and a catalyst is used to form a monomolecular film having cis-type polyacetylenic bonds.
Figure 7B:
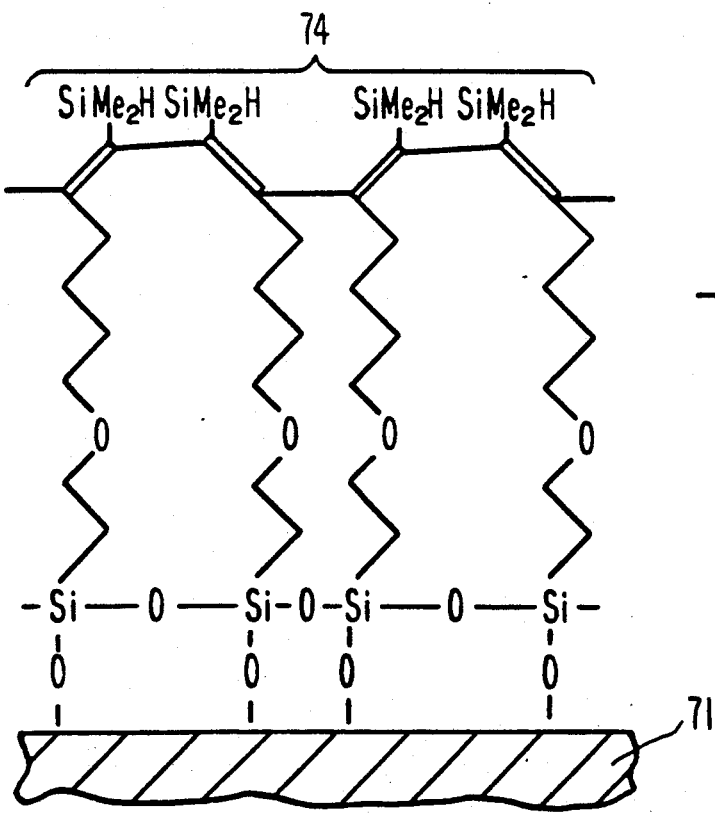

A monomolecular film was formed on a base plate 71 by the same procedure as in Example 17, using 6-AOS as a chemical adsorbent (See, FIG. 7a). The monomolecular film was exposed to an electron beam at a given interval in a certain direction to inactivate the acetylene group that was present in the exposed portion. Separately, a catalyst solution was prepared by dissolving a mixture of MoCl$_6$ (catalyst) and (C$_6$H$_5$)$_3$Bi (co-catalyst) in the molar ratio of 1:1 into anisole in a concentration of $2 \times 10^{-2}$ mol/L. The base plate having the monomolecular film formed as described above was immersed into the catalyst solution for 10 minutes a 25° C. to polymerize the remaining chemical adsorbent having the acetylene group, thereby forming a higher oriented monomolecular film having cis-type polyacetylenic lindages (see, FIG. 7b).

Example 22

A monomolecular film was formed on a base plate 81 by the same procedure as in Example 17 (See, FIGS. 8a–8c):

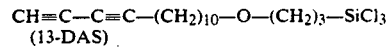

The monomolecular film was exposed to an electron beam at a given interval in a certain direction to inactivate the diacetylene group that was present in the exposed portion. Separately, a catalyst solution was prepared by dissolving TaCl$_5$ into toluene in a concentration of $2 \times 10^{-2}$ mol/L. The base plate having the monomolecular film formed as described above was immersed into the catalyst solution for 10 minutes at 25° C. to polymerize the remaining chemical adsorbent having the diacetylene group, thereby forming a higher oriented monomolecular film having trans-type polyacetylenic bonds (See, FIG. 8d).

Example 23

The monomolecular film having trans-type polyacetylenic bonds, prepared in Example 22, was irradiated with an electron beam, X-rays, or a gamma beam at the rate of 5 mJ/cm$^2$ to produce further polymerization, thereby forming a monomolecular film having polyacenic bonds with higher molecular orientation (See, FIG. 8e).

Examples 24–30

The procedures of Examples 17–23 were repeated except that the monomolecular film was rubbed in a certain direction instead of exposing it to an electron beam at a given interval in a certain direction to inactivate the acetylene or diacetylene groups that were present in the exposed portion.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A process for preparing an organic monomolecular film comprising:
   forming a monomolecular film on the surface of a base plate by adsorbing a chemical adsorbent having at least one triple bond, and a —SiCl group at one molecular end, and
   irradiating said monomolecular film with a high energy beam under an inert atmosphere to polymerize said chemical adsorbent at the triple bond, thereby forming a highly oriented conjugated polymer having polyacetylenic bonds.

2. A process of claim 1, wherein said chemical adsorbent is represented by the following formula I:

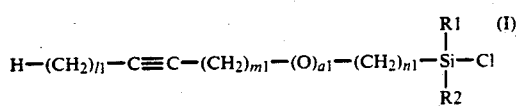

wherein R1 and R2 are each independently H, an alkyl or alkoxy group having 1 to 4 carbon atoms, or halogen; l1, m1 and n1 are 0 or larger integers; the sum of l1, m1 and n1 is from 5 to 25; and a1 is 0 or 1.

3. A process of claim 1, wherein said chemical adsorbent has a —SiH group or a —CH=CH$_2$ group at the other molecular end.

4. A process of claim 3, wherein said chemical adsorbent is represented by the following formula II:

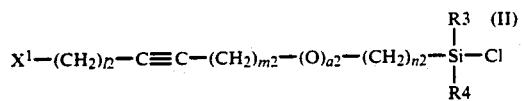

wherein said X$^1$ is

(R5 and R6 are each independently H, or an alkyl group having 1 to 4 carbon atoms), or CH$_2$=CH—; R3 and R4 are each independently H, an alkyl or alkoxy group having 1 to 4 carbon atoms, or halogen; l2, m2 and n2 are 0 or larger integers; the sum of 2, m2 and n2 is from 5 to 25; and a2 is 0 or 1.

5. A process for preparing an organic monomolecular film comprising:
   forming a monomolecular film on the surface of a base plate by adsorbing a chemical adsorbent having at least one triple bond, and a —SiCl group at one molecular end,
   selectively exposing the surface of said monomolecular film to an electron beam or X-rays, or carrying out a selective writing onto the surface of said film by the use of a Scanning Tunneling Microscope at a given interval in a certain direction to inactivate the triple bond of the chemical adsorbent adsorbed in the exposed portion, and
   irradiating said exposed or written monomolecular film with a high energy beam under an inert atmosphere to polymerize the remaining chemical adsorbent adsorbed in the unexposed portion, thereby forming a highly oriented conjugated polymer having polyacetylenic bonds.

6. A process of claim 5, wherein said chemical adsorbent is represented by the following formula I:

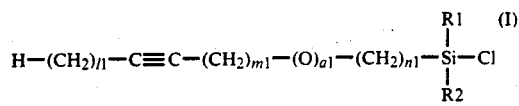

wherein R1 and R2 are each independently H, an alkyl or alkoxy group having 1 to 4 carbon atoms, or halogen; l1, m1 and n1 are 0 or larger integers; the sum of l1, m1 and n1 is from 5 to 25; and a1 is 0 or 1.

7. A process of claim 5, wherein said chemical adsorbent has a —SiH group or a —CH=CH$_2$ group at the other molecular end.

8. A process of claim 7, wherein said chemical adsorbent is represented by the following formula II:

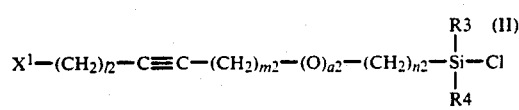

wherein said X$^1$ is

(R5 and R6 are each independently H, or an alkyl group having 1 to 4 carbon atoms), or CH$_2$=CH—; R3 and R4 are each independently H, an alkyl or alkoxy group having 1 to 4 carbon atoms, or halogen; l2, m2 and n2 are 0 or larger integers; the sum of l2, m2 and n2 is from 5 to 25; and a2 is 0 or 1.

9. A process for preparing an organic monomolecular film comprising:
   forming a monomolecular film on the surface of a base plate by adsorbing a chemical adsorbent having at least one triple bond, and a —SiCl group at one molecular end,
   rubbing said monomolecular film to orient said chemical adsorbent molecules, and
   irradiating said oriented monomolecular film with a high energy beam under an inert atmosphere to polymerize said chemical adsorbent at the triple bond, thereby forming a highly oriented conjugated polymer having polyacetylenic bonds.

10. A process of claim 9, wherein said chemical adsorbent is represented by the following formula I:

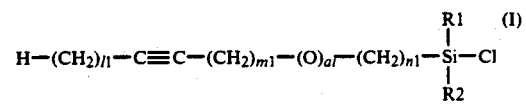

wherein R1 and R2 are each independently H, an alkyl or alkoxy group having 1 to 4 carbon atoms, or halogen; l1, m1 and n1 are 0 or larger integers; the sum of l1, m1 and n1 is from 5 to 25; and a1 is 0 or 1.

11. A process of claim 9, wherein said chemical adsorbent has a —SiH group or a —CH=CH₂ group at the other molecular end.

12. A process of claim 11, wherein said chemical adsorbent is represented by the following formula II:

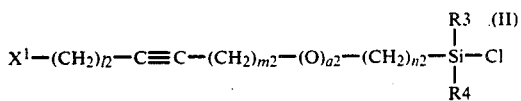

wherein said X¹ is

(R5 and R6 are each independently H, or an alkyl group having 1 to 4 carbon atoms), or CH₂=CH—; R3 and R4 are each independently H, an alkyl or alkoxy group having 1 to 4 carbon atoms, or halogen; l2, m2 and n2 are 0 or larger integers; the sum of l2, m2 and n2 is from 5 to 25; and a2 is 0 or 1.

13. A process for preparing an organic monomolecular film comprising:
forming a monomolecular film on the surface of a base plate by adsorbing a chemical adsorbent having a diacetylene group and a —SiCl group at one molecular end, and
irradiating said monomolecular film with a low energy beam to polymerize said chemical adsorbent at the diacetylene group, thereby forming a highly oriented conjugated polymer having polydiacetylenic bonds;
wherein said chemical adsorbent is represented by the following Formula III:

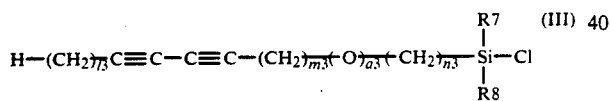

wherein R7 and R8 are each independently H, an alkyl or alkoxy group having 1 to 4 carbon atoms, or halogen; l3, m3 and n3 are 0 or larger integers, the sum of l3, m3 and n3 being from 5 to 25; and a3 is 0 or 1.

14. A process of claim 13, wherein said chemical adsorbent is any of the compounds represented by the following formula:

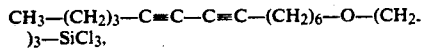

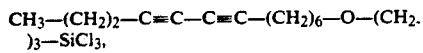

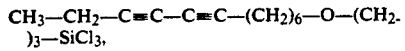

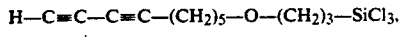

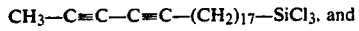

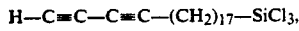

15. A process of claim 13, wherein said chemical adsorbent has a —SiH group or a —CH=CH₂ group at the other molecular end.

16. A process of claim 15, wherein said chemical adsorbent is represented by the following formula IV:

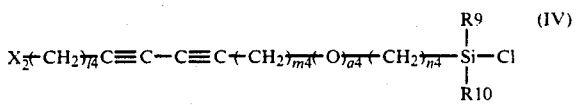

wherein said X² is

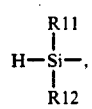

(R11 and R12 are each independently H, or an alkyl group having 1 to 4 carbon atoms), or CH₂=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

17. A process for preparing an organic monomolecular film comprising:
forming a monomolecular film on the surface of a base plate by adsorbing a chemical absorbent having a diacetylene group, and a —SiCl group at one molecular end,
selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, and
irradiating said exposed or written monomolecular film with a low energy beam under an inert atmosphere to polymerize the remaining chemical adsorbent adsorbed in the unexposed portion, thereby forming a highly oriented conjugated polymer having polydiacetylenic bonds;
wherein said chemical adsorbent is represented by the following Formula III:

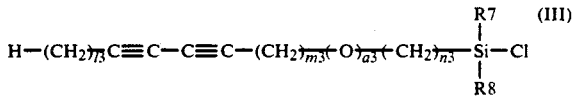

wherein R7 and R8 are each independently H, an alkyl or alkoxy group having 1 to 4 carbon atoms, or halogen; l3, m3 and n3 are 0 or larger integers, the sum of l3, m3 and n3 being from 5 to 25; and a3 is 0 or 1.

18. A process of claim 17, wherein said chemical adsorbent is any of the compounds represented by the following formula:

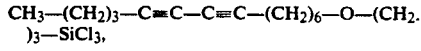

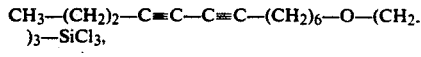

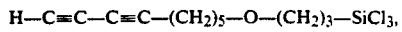

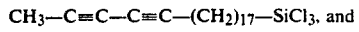

$H-C\equiv C-C\equiv C-(CH_2)_{17}-SiCl_3.$

19. A process of claim 17, wherein said chemical adsorbent has a —SiH group or a —CH=CH$_2$ group at the other molecular end.

20. A process of claim 17, wherein said chemical adsorbent is represented by the following formula IV:

$$X_2^1(CH_2)_{l4}C\equiv C-C\equiv C+CH_2)_{m4}(O)_{a4}(CH_2)_{n4}-\underset{\underset{R10}{|}}{\overset{\overset{R9}{|}}{Si}}-Cl \quad (IV)$$

wherein said X$^2$ is $$H-\underset{\underset{R12}{|}}{\overset{\overset{R11}{|}}{Si}}-,$$

(R11 and R12 are each independently H, or an alkyl group having 1 to 4 carbon atoms), or CH$_2$=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

21. A process for preparing an organic monomolecular film comprising:
forming a monomolecular film on the surface of a base plate by adsorbing a chemical absorbent having a diacetylene group, and a —SiCl group at one molecular end,
rubbing said monomolecular film to orient said chemical adsorbent molecules, and
irradiating said oriented monomolecular film with a low energy beam under an inert atmosphere to polymerize said chemical adsorbent at the diacetylene group, thereby forming a highly oriented conjugated polymer having polydiacetylenic bonds;
wherein said chemical adsorbent is represented by the following Formula III:

$$H-(CH_2)_{l3}C\equiv C-C\equiv C-(CH_2)_{m3}(O)_{a3}(CH_2)_{n3}-\underset{\underset{R8}{|}}{\overset{\overset{R7}{|}}{Si}}-Cl \quad (III)$$

wherein R7 and R8 are each independently H, an alkyl or alkoxy group having 1 to 4 carbon atoms, or halogen; l3, m3 and n3 are 0 or larger integers, the sum of l3, m3 and n3 being from 5 to 25; and a3 is 0 or 1.

22. A process of claim 21, wherein said chemical adsorbent is any of the compounds represented by the following formula:

CH$_3$—(CH$_2$)$_3$—C≡C—C≡C—(CH$_2$)$_6$—O—(CH$_2$)$_3$—SiCl$_3$,

CH$_3$—(CH$_2$)$_2$—C≡C—C≡C—(CH$_2$)$_6$—O—(CH$_2$)$_3$—SiCl$_3$,

CH$_3$—CH$_2$—C≡C—C≡C—(CH$_2$)$_6$—O—(CH$_2$)$_3$—SiCl$_3$,

H—C≡C—C≡C—(CH$_2$)$_5$—O—(CH$_2$)$_3$—SiCl$_3$,

CH$_3$—C≡C—C≡C—(CH$_2$)$_{17}$—SiCl$_3$, and

H—C≡C—C≡C—(CH$_2$)$_{17}$—SiCl$_3$.

23. A process of claim 21, wherein said chemical adsorbent has a —SiH group or a —CH=CH$_2$ group at the other molecular end.

24. A process of claim 23, wherein said chemical adsorbent is represented by the following formula IV:

$$X_2^2(CH_2)_{l4}C\equiv C-C\equiv C+CH_2)_{m4}(O)_{a4}(CH_2)_{n4}-\underset{\underset{R10}{|}}{\overset{\overset{R9}{|}}{Si}}-Cl \quad (IV)$$

wherein said X$^2$ is $$H-\underset{\underset{R12}{|}}{\overset{\overset{R11}{|}}{Si}}-,$$

(R11 and R12 are each independently H, or an alkyl group having 1 to 4 carbon atoms), or CH$_2$=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

25. A process for preparing an organic monomolecular film comprising:
forming a monomolecular film on the surface of a base plate by adsorbing a chemical adsorbent having a diacetylene group, and a —SiCl group at one molecular end, and
irradiating said monomolecular film with a high energy beam to polymerize said chemical adsorbent at the diacetylene group, thereby forming a highly oriented conjugated polymer having polyacetylenic or polydiacetylenic bonds.

26. A process of claim 25, wherein said chemical adsorbent is represented by the following formula III:

$$H-(CH_2)_{l3}C\equiv C-C\equiv C-(CH_2)_{m3}(O)_{a3}(CH_2)_{n3}-\underset{\underset{R8}{|}}{\overset{\overset{R7}{|}}{Si}}-Cl \quad (III)$$

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

27. A process of claim 26, wherein said chemical adsorbent is any of the compounds represented by the following formula:

CH$_3$—(CH$_2$)$_3$—C≡C—C≡C—(CH$_2$)$_6$—O—(CH$_2$)$_3$—SiCl$_3$,

CH$_3$—(CH$_2$)$_2$—C≡C—C≡C—(CH$_2$)$_6$—O—(CH$_2$)$_3$—SiCl$_3$,

CH$_3$—CH$_2$—C≡C—C≡C—(CH$_2$)$_6$—O—(CH$_2$)$_3$—SiCl$_3$,

H—C≡C—C≡C—(CH$_2$)$_5$—O—(CH$_2$)$_3$—SiCl$_3$,

CH$_3$—C≡C—C≡C—(CH$_2$)$_{17}$—SiCl$_3$, and

H—C≡C—C≡C—(CH$_2$)$_{17}$—SiCl$_3$.

28. A process of claim 25, wherein said chemical adsorbent has a —SiH group or a —CH=CH$_2$ group at the other molecular end.

29. A process of claim 28, wherein said chemical adsorbent is represented by the following formula IV:

$$X_2\text{+}CH_2\text{)}_{l4}\text{—}C\equiv C\text{—}C\equiv C\text{+}CH_2\text{)}_{m4}\text{+}O\text{)}_{a4}\text{+}CH_2\text{)}_{n4}\text{—}\underset{\underset{R10}{|}}{\overset{\overset{R9}{|}}{Si}}\text{—}Cl \quad (IV)$$

wherein said $X^2$ is $$H\text{—}\underset{\underset{R12}{|}}{\overset{\overset{R11}{|}}{Si}}\text{—},$$

(R11 and R12 are each independently H, or an alkyl group having 1 to 4 carbon atoms), or $CH_2=CH$—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

30. A process for preparing an organic monomolecular film comprising:

forming a monomolecular film on the surface of a base plate by adsorbing a chemical adsorbent having a diacetylene group, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, and irradiating said exposed or written monomolecular film with a high energy beam under an inert atmosphere to polymerize the remaining chemical adsorbent adsorbed in the unexposed portion, thereby forming a highly oriented conjugated polymer having polyacetylenic or polydiacetylenic bonds.

31. A process of claim 30, wherein said chemical adsorbent is represented by the following formula III:

$$H\text{+}CH_2\text{)}_{l3}\text{—}C\equiv C\text{—}C\equiv C\text{+}CH_2\text{)}_{m3}\text{+}O\text{)}_{a3}\text{+}CH_2\text{)}_{n3}\text{—}\underset{\underset{R8}{|}}{\overset{\overset{R7}{|}}{Si}}\text{—}Cl \quad (III)$$

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

32. A process of claim 31, wherein said chemical adsorbent is any of the compounds represented by the following formula:

$CH_3\text{—}(CH_2)_2\text{—}C\equiv C\text{—}C\equiv C\text{—}(CH_2)_6\text{—}O\text{—}(CH_2)_3\text{—}SiCl_3$, $CH_3\text{—}CH_2\text{—}C\equiv C\text{—}C\equiv C\text{—}(CH_2)_6\text{—}O\text{—}(CH_2)_3\text{—}SiCl_3$, $CH_3\text{—}CH_2\text{—}C\equiv C\text{—}(CH_2)_6\text{—}O\text{—}(CH_2)_3\text{—}SiCl_3$, $H\text{—}C\equiv C\text{—}C\equiv C\text{—}(CH_2)_5\text{—}O\text{—}(CH_2)_3\text{—}SiCl_3$, $CH_3\text{—}C\equiv C\text{—}C\equiv C\text{—}(CH_2)_{17}\text{—}SiCl_3$, and $H\text{—}C\equiv C\text{—}C\equiv C\text{—}(CH_2)_{17}\text{—}SiCl_3$.

33. A process of claim 30, wherein said chemical adsorbent has a —SiH group or a —CH=CH₂ group at the other molecular end.

34. A process of claim 33, wherein said chemical adsorbent is represented by the following formula (IV):

$$X_2\text{+}CH_2\text{)}_{l4}\text{—}C\equiv C\text{—}C\equiv C\text{+}CH_2\text{)}_{m4}\text{—}(O)_{a4}\text{+}CH_2\text{)}_{n4}\text{—}\underset{\underset{R10}{|}}{\overset{\overset{R9}{|}}{Si}}\text{—}Cl \quad (IV)$$

wherein said $X^2$ is $$H\text{—}\underset{\underset{R12}{|}}{\overset{\overset{R11}{|}}{Si}}\text{—},$$

(R11 and R12 are each independently H, or an alkyl group having 1 to 4 carbon atoms), or $CH_2=CH$—; R9 and R10 are each independently H, an alkyl or alkoxyl group having 1 to 4 carbon atoms, or halogen; l4, m4 and n4 are 0 or larger integers; the sum of l4, m4 and n4 is from 5 to 25; and a4 is 0 or 1.

35. A process for preparing an organic monomolecular film comprising:

forming a monomolecular film on the surface of a base plate by adsorbing a chemical adsorbent having a diacetylene group, and a —SiCl group at one molecular end, rubbing said monomolecular film to orient said chemical adsorbent molecules, and irradiating said oriented monomolecular film with a high energy beam under an inert atmosphere to polymerize said chemical adsorbent at the diacetylene group, thereby forming a highly oriented conjugated polymer having polyacetylenic or polydiacetylenic bonds.

36. A process of claim 35, wherein said chemical adsorbent is represented by the following formula III:

$$H\text{+}CH_2\text{)}_{l3}\text{—}C\equiv C\text{—}C\equiv C\text{+}CH_2\text{)}_{m3}\text{+}O\text{)}_{a3}\text{+}CH_2\text{)}_{n3}\text{—}\underset{\underset{R8}{|}}{\overset{\overset{R7}{|}}{Si}}\text{—}Cl \quad (III)$$

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

37. A process of claim 36, wherein said chemical adsorbent is any of the compounds represented by the following formula:

$CH_3\text{—}(CH_2)_3\text{—}C\equiv C\text{—}C\equiv C\text{—}(CH_2)_6\text{—}O\text{—}(CH_2)_3\text{—}SiCl_3$, $CH_3\text{—}(CH_2)_2\text{—}C\equiv C\text{—}C\equiv C\text{—}(CH_2)_6\text{—}O\text{—}(CH_2)_3\text{—}SiCl_3$, $CH_3\text{—}CH_2\text{—}C\equiv C\text{—}C\equiv C\text{—}(CH_2)_6\text{—}O\text{—}(CH_2)_3\text{—}SiCl_3$, $H\text{—}C\equiv C\text{—}C\equiv C\text{—}(CH_2)_5\text{—}O\text{—}(CH_2)_3\text{—}SiCl_3$, $CH_3\text{—}C\equiv C\text{—}C\equiv C\text{—}(CH_2)_{17}\text{—}SiCl_3$, and $H\text{—}C\equiv C\text{—}C\equiv C\text{—}(CH_2)_{17}\text{—}SiCl_3$.

38. A process of claim 35, wherein said chemical adsorbent has a —SiH group or a —CH=CH₂ group at the other molecular end.

39. A process of claim 38, wherein said chemical adsorbent is represented by the following formula IV:

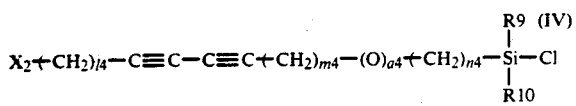

wherein said $X^2$ is

(R11 and R12 are each independently H, or an alkyl group having 1 to 4 carbon atoms), or $CH_2=CH-$; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

40. A process for preparing an organic monomolecular film comprising:

forming a monomolecular film on the surface of a base plate by adsorbing a chemical adsorbent having at least one triple bond, and a —SiCl group at one molecular end, subjecting said monomolecular film to come into contact with a metal compound catalyst dissolved in an organic solvent to polymerize said chemical adsorbent at the triple bond, thereby forming a highly oriented conjugated polymer having a polyacetylenic bonds.

41. A process of claim 40, wherein said chemical adsorbent is represented by the following formula I:

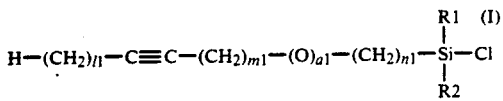

wherein R1 and R2 are each independently H, an alkyl or alkoxyl group having 1 to 4 carbon atoms, or halogen; l1, m1 and n1 are 0 or larger integers; the sum of l1, m1 and n1 is from 5 to 25; and a1 is 0 or 1.

42. A process of claim 40, wherein said chemical adsorbent has a —SiH group or a —CH=CH$_2$ group at the other molecular end.

43. A process of claim 42, wherein said chemical adsorbent is represented by the following formula II:

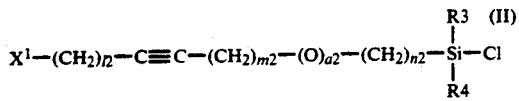

wherein said $X^1$ is

(R5 and R6 are each independently H, or an alkyl group having 1 to 4 carbon atoms), or $CH_2=CH-$; R3 and R4 are each independently H, an alkyl or alkoxy group having 1 to 4 carbon atoms, or halogen; l2, m2 and n2 are 0 or larger integers; the sum of l2, m2 and n2 is from 5 to 25; and a2 is 0 or 1.

44. A process of claim 40, wherein said metal compound contains Mo, W or Ta.

45. A process of claim 40, wherein an organic tin or organic bismuth compound is used as a co-catalyst.

46. A process of claim 44, wherein said metal compound is $MoCl_5$, said organic solvent has at least one oxygen atom in its own molecule, and said polyacetylenic bond has a cis-type structure.

47. A process for preparing an organic monomolecular film comprising:

forming a monomolecular film on the surface of a base plate by adsorbing a chemical adsorbent having at least one triple bond, and a —SiCl group at one molecular end, selectively exposing the surface of said monomolecular film to an electron beam or X-rays, or carrying out a selective writing onto the surface of said film by the use of a Scanning Tunneling Microscope at a given interval in a certain direction to inactivate the triple bond of the chemical adsorbent adsorbed in the exposed portion, and subjecting said monomolecular film to come into contact with a metal compound catalyst dissolved in an organic solvent to polymerize the remaining chemical adsorbent adsorbed in the unexposed portion, thereby forming a highly oriented conjugated polymer having polyacetylenic bonds.

48. A process of claim 47, wherein said chemical adsorbent is represented by the following formula I:

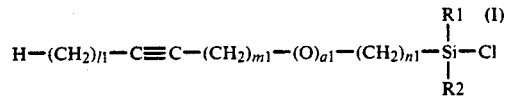

wherein R1 and R2 are each independently H, an alkyl or alkoxy group having 1 to 4 carbon atoms, or halogen; l1, m1 and n1 are 0 or larger integers; the sum of l1, m1 and n1 is from 5 to 25; and a1 is 0 or 1.

49. A process of claim 47, wherein said chemical adsorbent has a —SiH group or a —CH=CH$_2$ group at the other molecular end.

50. A process of claim 49, wherein said chemical adsorbent is represented by the following formula II:

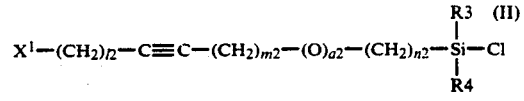

wherein said $X^1$ is

(R5 and R6 are each independently H, or an alkyl group having 1 to 4 carbon atoms), or $CH_2=CH-$; R3 and R4 are each independently H, an alkyl or alkoxy group having 1 to 4 carbon atoms, or halogen; l2, m2 and n2 are 0 or larger integers; the sum of l2, m2 and n2 is from 5 to 25; and a2 is 0 or 1.

51. A process of claim 47, wherein said metal compound contains Mo, W or Ta.

52. A process of claim 47, wherein an organic tin or organic bismuth compound is used as a co-catalyst.

53. A process of claim 52, wherein said metal compound is $MoCl_5$, said organic solvent has at least one oxygen in its own molecule, and said polyacetylenic bond has a cis-type structure.

54. A process for preparing an organic monomolecular film comprising:
  forming a monomolecular film on the surface of a base plate by adsorbing a chemical adsorbent having at least one triple bond, and a —SiCl group at one molecular end,
  rubbing said monomolecular film to orient said chemical adsorbent molecules, and
  subjecting said monomolecular film to come into contact with a metal compound catalyst dissolved in an organic solvent to polymerize said chemical adsorbent at the triple bond, thereby forming a highly oriented conjugated polymer having a polyacetylenic bonds.

55. A process of claim 54, wherein said chemical adsorbent is represented by the following formula I:

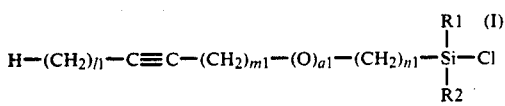

wherein R1 and R2 are each independently H, an alkyl or alkoxy group having 1 to 4 carbon atoms, or halogen; l1, m1 and n1 are 0 or larger integers; the sum of l1, m1 and n1 is from 5 to 25; and a1 is 0 or 1.

56. A process of claim 54, wherein said chemical adsorbent has a —SiH group or a —CH=CH2 group at the other molecular end.

57. A process of claim 56, wherein said chemical adsorbent is represented by the following formula II:

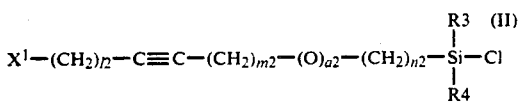

wherein said $X^1$ is

(R5 and R6 are each independently H, or an alkyl group having 1 to 4 carbon atoms), or CH2=CH—; R3 and R4 are each independently H, an alkyl or alkoxy group having 1 to 4 carbon atoms, or halogen; l2, m2 and n2 are 0 or larger integers; the sum of l2, m2 and n2 is from 5 to 25; and a2 is 0 or 1.

58. A process of claim 54, wherein said metal compound contains Mo, W or Ta.

59. A process of claim 54, wherein an organic tin or organic bismuth compound is used as a co-catalyst.

60. A process of claim 58, wherein said metal compound is $MoCl_5$, said organic solvent has at least one oxygen in its own molecule, and said polyacetylenic bond has a cis-type structure.

61. A process for preparing an organic monomolecular film comprising:
  forming a monomolecular film on the surface of a base plate by adsorbing a chemical adsorbent having a diacetylene group, and a —SiCl group at one molecular end, and
  subjecting said monomolecular film to come into contact with a metal compound catalyst dissolved in an organic solvent to polymerize said chemical adsorbent at the diacetylene group, thereby forming a highly oriented conjugated polymer having polyacetylenic bonds.

62. A process of claim 61, wherein said chemical adsorbent is represented by the following formula III:

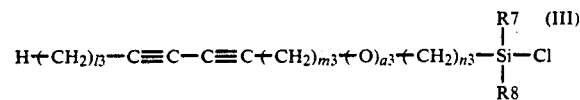

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

63. A process of claim 62, wherein said chemical adsorbent is any of the compounds represented by the following formula:

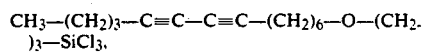

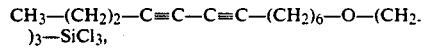

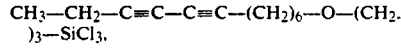

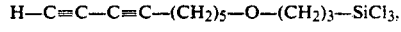

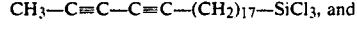

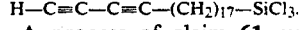

64. A process of claim 61, wherein said chemical adsorbent has a —SiH group or a —CH=CH2 group at the other molecular end.

65. A process of claim 64, wherein said chemical adsorbent is represented by the following formula IV:

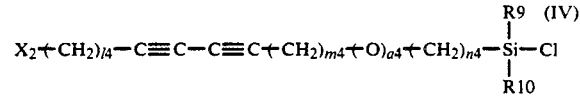

wherein said $X^2$ is

(R11 and R12 are each independently H, or an alkyl group having 1 to 4 carbon atoms), or CH2=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

66. A process of claim 61, wherein said metal compound contains Mo, W or Ta.

67. A process of claim 61, wherein an organic tin or organic bismuth compound is used as a co-catalyst.

68. A process of claim 67, wherein said metal compound is $MoCl_5$, said organic solvent has at least one oxygen in its own molecule, and said polyacetylenic bond has a cis-type structure.

69. A process for preparing an organic monomolecular film comprising:
   forming a monomolecular film on the surface of a base plate by adsorbing a chemical adsorbent having a diacetylene group, and a —SiCl group at one molecular end,
   selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion, and
   subjecting said exposed monomolecular film to come into contact with a metal compound catalyst dissolved in an organic solvent to polymerize the remaining chemical adsorbent adsorbed in the unexposed portion, thereby forming a highly oriented conjugated polymer having polyacetylenic bonds.

70. A process of claim 69, wherein said chemical adsorbent is represented by the following formula III:

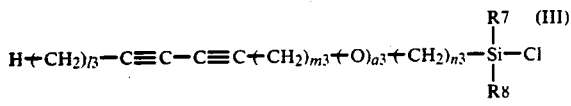

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

71. A process of claim 70, wherein said chemical adsorbent is any of the compounds represented by the following formula:

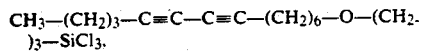
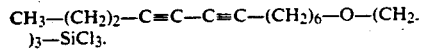
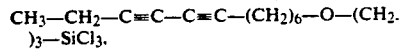
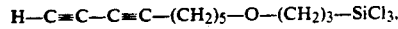
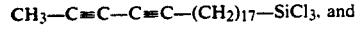
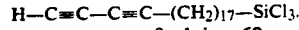

72. A process of claim 69, wherein said chemical adsorbent has a —SiH group or a —CH=CH2 group at the other molecular end.

73. A process of claim 72, wherein said chemical adsorbent is represented by the following formula IV:

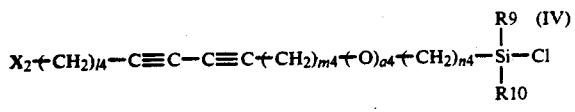

wherein said X² is

(R11 and R12 are each independently H, or an alkyl group having 1 to 4 carbon atoms), or CH2=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

74. A process of claim 69, wherein said metal compound contains Mo, W or Ta.

75. A process of claim 69, wherein an organic tin or organic bismuth compound is used as a co-catalyst.

76. A process of claim 74, wherein said metal compound is MoCl5, said organic solvent has at least one oxygen in its own molecule, and said polyacetylenic bond has a cis-type structure.

77. A process for preparing an organic monomolecular film comprising:
   forming a monomolecular film on the surface of a base plate by adsorbing a chemical adsorbent having a diacetylene group, and a —SiCl group at one molecular end,
   rubbing said monomolecular film to orient said chemical adsorbent molecules, and
   subjecting said oriented monomolecular film to come into contact with a metal compound catalyst dissolved in an organic solvent to polymerize said chemical adsorbent at the diacetylene group, thereby forming a highly oriented conjugated polymer having polyacetylenic bonds.

78. A process of claim 77, wherein said chemical adsorbent is represented by the following formula III:

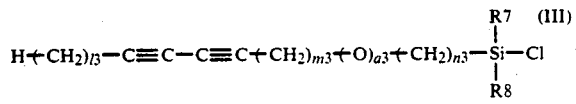

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

79. A process of claim 78, wherein said chemical adsorbent is any of the compounds represented by the following formula:

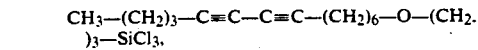
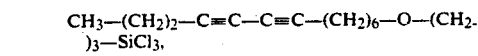
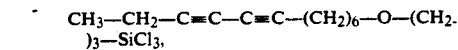
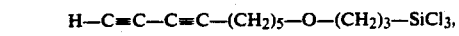
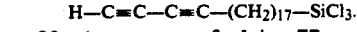

80. A process of claim 77, wherein said chemical adsorbent has a —SiH group or a —CH=CH2 group at the other molecular end.

81. A process of claim 80, wherein said chemical adsorbent is represented by the following formula IV:

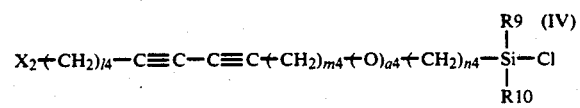

wherein said X² is

(R11 and R12 are each independently H, or an alkyl group having 1 to 4 carbon atoms), or $CH_2=CH-$; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

82. A process of claim 77, wherein said metal compound contains Mo, W or Ta.

83. A process of claim 77, wherein an organic tin or organic bismuth compound is used as a co-catalyst.

84. A process of claim 77, wherein said metal compound is $MoCl_5$, said organic solvent has at least one oxygen in its own molecule, and said polyacetylenic bond has a cis-type structure.

85. A process for preparing an organic monomolecular film comprising:
   forming a monomolecular fil,m on the surface of a base plate by adsorbing a chemical adsorbent having a diacetylene group, and a —SiCl group at one molecular end,
   subjecting said monomolecular film to come into contact with a metal compound catalyst dissolved in an organic solvent to polymerize said chemical adsorbent at the diacetylene group, thereby forming a polyacetylenic bonds in trans configuration,
   irradiating said catalyst-treated monomolecular film with a high energy beam under an inert atmosphere to produce further polymerization, thereby forming a highly oriented polyacene-type conjugated polymer.

86. A process of claim 85, wherein said chemical adsorbent is represented by the following formula III:

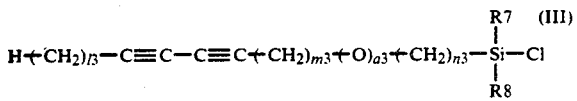

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

87. A process of claim 86, wherein said chemical adsorbent is any of the compounds represented by the following formula:

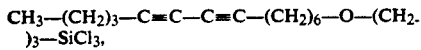
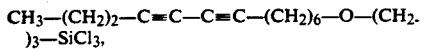
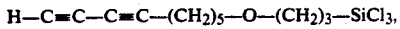
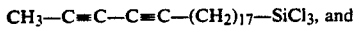
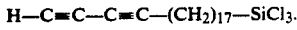

88. A process of claim 85, wherein said chemical adsorbent has a —SiH group or a —CH=CH$_2$ group at the other molecular end.

89. A process of claim 88, wherein said chemical adsorbent is represented by the following formula IV:

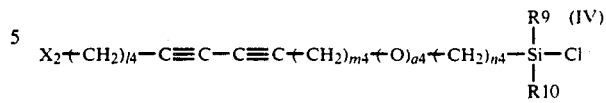

wherein said $X^2$ is

(R11 and R12 are each independently H, or an alkyl group having 1 to 4 carbon atoms), or $CH_2=CH-$; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

90. A process of claim 85, wherein said metal compound contains Mo, W or Ta.

91. A process of claim 85, wherein an organic tin or organic bismuth compound is used as a co-catalyst.

92. A process for preparing an organic monomolecular film comprising:
   forming a monomolecular film on the surface of a base plate by adsorbing a chemical adsorbent having a diacetylene group, and a —SiCl group at one molecular end,
   selectively exposing the surface of said monomolecular film to an electron beam or X-rays, or carrying out a selective writing onto the surface of said film by the use of a Scanning Tunneling Microscope at a given interval in a certain direction to inactivate the diacetylene group of the chemical adsorbent adsorbed in the exposed portion,
   subjecting said exposed monomolecular film to come into contact with a metal compound catalyst dissolved in an organic solvent to polymerize the remaining chemical adsorbent adsorbed in the unexposed portion, thereby forming a polyacetylenic bonds in trans configuration, and
   irradiating said catalyst-treated monomolecular film with a high energy beam under an inert atmosphere to produce further polymerization, thereby forming a highly oriented polyacene-type conjugated polymer.

93. A process of claim 92, wherein said chemical adsorbent is represented by the following formula III:

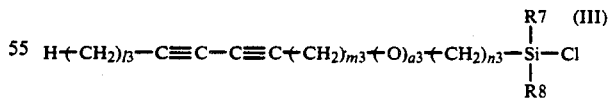

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

94. A process of claim 93, wherein said chemical adsorbent is any of the compounds represented by the following formula:

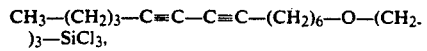

$CH_3-(CH_2)_2-C\equiv C-C\equiv C-(CH_2)_6-O-(CH_2)_3-SiCl_3,$ $CH_3-CH_2-C\equiv C-C\equiv C-(CH_2)_6-O-(CH_2)_3-SiCl_3,$ $H-C\equiv C-C\equiv C-(CH_2)_5-O-(CH_2)_3-SiCl_3,$ $CH_3-C\equiv C-C\equiv C-(CH_2)_{17}-SiCl_3,$ and $H-C\equiv C-C\equiv C-(CH_2)_{17}-SiCl_3.$ 95. A process of claim 93, wherein said chemical adsorbent has a —SiH group or a —CH=CH$_2$ group at the other molecular end.

96. A process of claim 93, wherein said chemical adsorbent is represented by the following formula IV:

$$X_2(CH_2)_{l4}-C\equiv C-C\equiv C(CH_2)_{m4}(O)_{a4}(CH_2)_{n4}-\underset{R10}{\overset{R9}{\underset{|}{\overset{|}{Si}}}}-Cl \quad (IV)$$

wherein said X$^2$ is $$H-\underset{R12}{\overset{R11}{\underset{|}{\overset{|}{Si}}}}-.$$

(R11 and R12 are each independently H, or an alkyl group having 1 to 4 carbon atoms), or CH$_2$=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

97. A process of claim 92, wherein said metal compound contains Mo, W or Ta.

98. A process of claim 92, wherein an organic tin or organic bismuth compound is used as a co-catalyst.

99. A process for preparing an organic monomolecular film comprising:
  forming a monomolecular film on the surface of a base plate by adsorbing a chemical adsorbent having a diacetylene group, and a —SiCl group at one molecular end,
  rubbing said monomolecular film to orient said chemical adsorbent molecules,
  subjecting said oriented monomolecular film to come into contact with a metal compound catalyst dissolved in an organic solvent to polymerize said chemical adsorbent at the diacetylene group, thereby forming polyacetylenic bonds in trans configuration. and
  irradiating said catalyst-treated monomolecular film with a high energy beam under an inactive atmosphere to produce further polymerization, thereby forming a highly oriented polyacene-type conjugated polymer.

100. A process of claim 99, wherein said chemical adsorbent is represented by the following formula III:

$$H(CH_2)_{l3}-C\equiv C-C\equiv C(CH_2)_{m3}(O)_{a3}(CH_2)_{n3}-\underset{R8}{\overset{R7}{\underset{|}{\overset{|}{Si}}}}-Cl \quad (III)$$

wherein R7 and R8 are each independently H, an alkyl or alkoxy group having 1 to 4 carbon atoms, or halogen; l3, m3 and n3 are 0 or larger integers; the sum of l3, m3 and n3 is from 5 to 25; and a3 is 0 or 1.

101. A process of claim 100, wherein said chemical adsorbent is any of the compounds represented by the following formula:

$CH_3-(CH_2)_3-C\equiv C-C\equiv C-(CH_2)_6-O-(CH_2)_3-SiCl_3,$ $CH_3-(CH_2)_2-C\equiv C-C\equiv C-(CH_2)_6-O-(CH_2)_3-SiCl_3,$ $CH_3-CH_2-C\equiv C-C\equiv C-(CH_2)_6-O-(CH_2)_3-SiCl_3,$ $H-C\equiv C-C\equiv C-(CH_2)_5-O-(CH_2)_3-SiCl_3,$ $CH_3C\equiv C-C\equiv C-(CH_2)_{17}-SiCl_3.$ and $H-C\equiv C-C\equiv C-(CH_2)_{17}-SiCl_3.$ 102. A process of claim 99, wherein said chemical adsorbent has a —SiH group or a —CH=CH$_2$ group at the other molecular end.

103. A process of claim 102, wherein said chemical adsorbent is represented by the following formula IV:

$$X_2(CH_2)_{l4}-C\equiv C-C\equiv C(CH_2)_{m4}(O)_{a4}(CH_2)_{n4}-\underset{R10}{\overset{R9}{\underset{|}{\overset{|}{Si}}}}-Cl \quad (IV)$$

wherein said X$^2$ is $$H-\underset{R12}{\overset{R11}{\underset{|}{\overset{|}{Si}}}}-,$$

(R11 and R12 are each independently H, or an alkyl group having 1 to 4 carbon atoms), or CH$_2$=CH—; R9 and R10 are each independently H, an alkyl or alkoxy group having 1 to 4 carbon atoms, or halogen; l4, m4 and n4 are 0 or larger integers; the sum of l4, m4 and n4 is from 5 to 25; and a4 is 0 or 1.

104. A process of claim 99, wherein said metal compound contains Mo, W or Ta.

105. A process of claim 99, wherein an organic tin or organic bismuth compound is used as a co-catalyst.

* * * * *